United States Patent
Scott et al.

(10) Patent No.: US 8,343,157 B2
(45) Date of Patent: Jan. 1, 2013

(54) BONE-REAMING SYSTEM

(75) Inventors: Christopher Scott, Hackensack, NJ (US); Joseph C. Jenkins, II, Lindenhurst, NY (US); Rodney P. Johnson, Highland Lakes, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1618 days.

(21) Appl. No.: 11/807,210

(22) Filed: May 25, 2007

(65) Prior Publication Data

US 2008/0294169 A1 Nov. 27, 2008

(51) Int. Cl.
*A61B 17/00* (2006.01)
(52) U.S. Cl. ............................................ 606/80
(58) Field of Classification Search .............. 606/79–81, 606/86 R, 91
See application file for complete search history.

(56) References Cited

U.S. PATENT DOCUMENTS

| | | | |
|---|---|---|---|
| 3,112,743 A | 12/1963 | Cochran et al. | |
| 3,173,417 A | 3/1965 | Guillant | |
| 4,802,468 A | 2/1989 | Powlan | |
| 6,309,394 B1 | 10/2001 | Staehlin et al. | |
| 6,364,910 B1 * | 4/2002 | Shultz et al. | 623/19.13 |
| 6,488,686 B2 | 12/2002 | Staehlin et al. | |
| 6,491,692 B1 | 12/2002 | Meislin et al. | |
| 6,530,927 B2 | 3/2003 | Staehlin et al. | |
| 6,723,102 B2 | 4/2004 | Johnson et al. | |
| 6,755,865 B2 | 6/2004 | Tarabishy | |
| 6,761,723 B2 | 7/2004 | Buttermann et al. | |
| 2001/0034525 A1 | 10/2001 | Staehlin et al. | |
| 2001/0034533 A1 | 10/2001 | Staehlin et al. | |
| 2002/0151901 A1 | 10/2002 | Bryan et al. | |
| 2002/0193797 A1 | 12/2002 | Johnson et al. | |
| 2003/0055431 A1 | 3/2003 | Brannon | |
| 2003/0060889 A1 | 3/2003 | Tarabishy | |
| 2003/0060890 A1 | 3/2003 | Tarabishy | |
| 2003/0236523 A1 | 12/2003 | Johnson et al. | |
| 2004/0138670 A1 | 7/2004 | Metzger | |
| 2004/0167516 A1 | 8/2004 | Cucin | |
| 2005/0027299 A1 | 2/2005 | Metzger | |
| 2005/0049601 A1 | 3/2005 | Keller | |
| 2005/0154398 A1 | 7/2005 | Miniaci et al. | |
| 2005/0171553 A1 | 8/2005 | Schwarz et al. | |
| 2005/0234464 A1 | 10/2005 | Brannon | |
| 2006/0020282 A1 | 1/2006 | Henniges et al. | |
| 2006/0041268 A1 | 2/2006 | Shores et al. | |
| 2006/0058886 A1 * | 3/2006 | Wozencroft | 623/22.15 |
| 2006/0085006 A1 | 4/2006 | Ek et al. | |
| 2006/0189989 A1 * | 8/2006 | Bert | 606/69 |
| 2007/0010822 A1 * | 1/2007 | Zalenski et al. | 606/79 |

* cited by examiner

*Primary Examiner* — Kevin T Truong
*Assistant Examiner* — Michael Araj
(74) *Attorney, Agent, or Firm* — Lerner, David, Littenberg, Krumholz & Mentlik, LLP

(57) ABSTRACT

A bone-reaming system for use in bone cavities which allows for a less invasive and more precise surgical procedure is disclosed. An apparatus according to such a system may include a housing, a motor disposed within the housing, and a cutter attached to the motor and extendable through the aperture, wherein the housing is capable of articulating with respect to a bone cavity so as to allow the cutter to cut at least a portion of the bone cavity. A routing guide is used in conjunction with the apparatus to provide a template through which to cut preselected portions of a bone cavity. Also disclosed is a method for using such a bone-reaming system.

26 Claims, 23 Drawing Sheets

BONE-REAMING SYSTEM

BACKGROUND OF THE INVENTION

The present invention relates to a bone-reaming system, and more particularly, to an apparatus and method for cutting select portions of a bone cavity through the use of a removable guide and a motor-driven cutter which both fit substantially within the body of a patient.

Orthopedic surgery has become more and more prevalent in recent years. Some of the more popular surgical procedures in this area involve the total or partial replacement of joints. Often, this is required because of the wearing or degeneration of cartilage within the joint space. As this cartilage typically provides an articulation surface for two adjacent bones, such wearing or degeneration often causes severe pain in a patient. Thus, it has become common place for some or all of the cartilage (and even some bone) to be removed and/or replaced with different orthopedic implants. For example, one joint which is often the subject of one or more surgeries in a patient is the hip. The ball and socket created by the head of the femur and the acetabulum, respectively, tends to wear during the life of a patient. A surgical procedure on this joint typically involves resurfacing or removing the femoral head and resurfacing the acetabulum. In addition, other smaller areas may be targeted during a procedure.

Often the position and orientation of a ball and socket joint, such as the hip or shoulder, within the body make it difficult to effectively operate without an invasive dislocation of the joint. Such a dislocation may irreversibly damage the joint capsule as well as many of the ligaments and tendons attached to and/or around the joint. In addition, the ball and socket portions of a bone are not meant to be dislocated, and so irreparable harm to the bone surfaces of each may also occur from such dislocation.

In some cases, when surgery is necessary on the hip joint, only the acetabulum, and not the femur, may be damaged. If the femoral head and neck are healthy, they require little to no surgical steps and merely become obstacles blocking access to the acetabulum. Even if they are in fact damaged, the remaining femoral structure may also not be useful during operation in or on the acetabulum. For example, when the femur is healthy, it is often removed from the acetabulum before surgery is performed on the socket. In order to avoid major damage to the hip socket, it is possible to move the femoral head a small distance relative to the acetabulum to gain access to the damaged socket. Still, in this situation it is difficult to reach the necessary portions of the acetabulum with any precision because the femoral head is positioned to block the insertion and/or use of a surgical instrument. Penetration into or removal of any portion of the femur in this instance, though it may aid in the surgery on the acetabulum, is not always an option.

Nonetheless, often the need for operation on the acetabulum is accompanied by damage to the femur. As such, a portion of the femur may need to be removed as a part of the same procedure. Although techniques have been developed to use the remaining portion of the femur to aid in the reaming of the acetabulum, the integrity of the femur may not be able to handle such manipulation and force. An example of such a technique is disclosed in U.S. Pat. No. 6,723,102 to Johnson et al. ("Johnson"), which teaches sculpting a bone surface of a first bone while anchoring the bone sculpting tool in an adjacent bone with which the first bone normally articulates. Johnson requires a two-bone system where the bones articulate with one another. The adjacent bone is used to mount the bone sculpting tool, with the figures of Johnson illustrating a complete removal of the femoral head to do so. Even if the femoral head is not removed, a relatively large separation between the ball and socket is necessary to mount such a device to articulate with the first bone. Thus, for surgery on a bone socket which does not require additional medical attention directed to the mating ball, this technique is overly invasive.

Repair of small or focal defects in cartilage is something which also may be desired. The general thought surrounding this technique is to repair only worn portions of cartilage, rather than removing entire cartilage surfaces. Of course, this adds another wrinkle to the preparation of a particular site. In contrast to utilizing relatively large devices to remove an entire cartilage surface, smaller cutters or reamers are desired. To this point such devices have not lent themselves to the preparation of site within a bone cavity, such as a socket of a ball and socket joint.

Therefore, there exists a need for an apparatus for use in a surgical procedure on a bone socket that is minimally invasive and allows for increased precision. A need also exists for an apparatus that may operate on predefined portions of a bone socket without the need for a direct view to the surgical site, and one which can be utilized in connection with repair of focal defects.

SUMMARY OF THE INVENTION

A first aspect of the present invention is a bone-reaming apparatus. Certain embodiments of this first aspect include a housing having an aperture and an articulation surface, a motor disposed within the housing and a cutter attached to the motor and extendable through the aperture, the cutter having a cutter surface smaller than the articulation surface. Preferably, the articulation surface of the housing is capable of articulating with respect to a bone cavity so as to allow the cutter to cut at least a portion of the bone cavity.

In other embodiments of the first aspect, the bone-reaming apparatus may include a motor which is moveable within the housing. The cutter may be slidably connected to the motor. Additionally, the motor preferably translates power through a single axial shaft to the cutter. The cutter may selected from the group consisting of a drill bit, a burr, one or more blades, and one or more laterally-moving blades. In certain embodiments, the housing may be substantially spherical in shape, or substantially cubic in shape. In addition, the apparatus may include a handle integrally connected to the housing or connected at a connection. The connection may allow for a pivotable or other moveable relationship between the handle and the housing. The handle may include a grip and a stem, and the grip may further include a knurled or rubber surface.

A second aspect of the present invention is a bone-reaming system. Such a system may include a cutting apparatus including a housing having an aperture, a motor disposed within the housing, and a cutter attached to the motor and extendable through the aperture. Further, the system may include a routing guide having at least one cutout, where the routing guide is preferably capable of being disposed within a bone cavity and the housing is capable of articulating with respect to the routing guide so as to allow the cutter to cut at least a portion of the bone cavity through the at least one cutout.

Other embodiments of this second aspect may include a cutting apparatus further including a handle connected to the housing at a connection. The connection may allow for a pivotable or other moveable relationship between the handle and the housing. Alternatively, a handle may be formed integrally with the housing. Preferably, the motor translates power through a single axial shaft to the cutter. The cutter may be selected from the group consisting of a drill bit, a burr, one or more blades, and one or more laterally-moving blades. In certain embodiments, the housing may be substantially spherical in shape or substantially cubic in shape. In addition, the routing guide may include a stabilization means, with such means being selected from the group consisting of spikes, screws, nails, cement or an adhesive. Preferably, the system may also include a power supply and connection between the power supply and the motor. In one preferred embodiment, the cutting apparatus and the routing guide are adapted for cutting at least a portion of an acetabulum.

A third aspect of the present invention is a method of resurfacing a bone. Such method may include the steps of providing a cutting apparatus comprising a housing having an aperture, a motor disposed within the housing, and a cutter attached to the motor and extendable through the aperture, providing a routing guide having at least one cutout, removably securing the routing guide to a bone cavity, inserting the cutting apparatus into the routing guide, so that at least a portion of the housing contacts the routing guide, and manipulating the cutting apparatus within the routing guide to allow the cutter to cut at least a portion of the bone cavity.

Other embodiments of this third aspect may include the step of removing the routing guide and the cutting apparatus and/or the step of anchoring the routing guide with a stabilization means. Preferably, the housing is rotatable within the routing guide. The manipulating step may include articulating a housing having a convex surface within a routing guide having a complementary concave surface. This may further involve a bone cavity having a concave surface.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
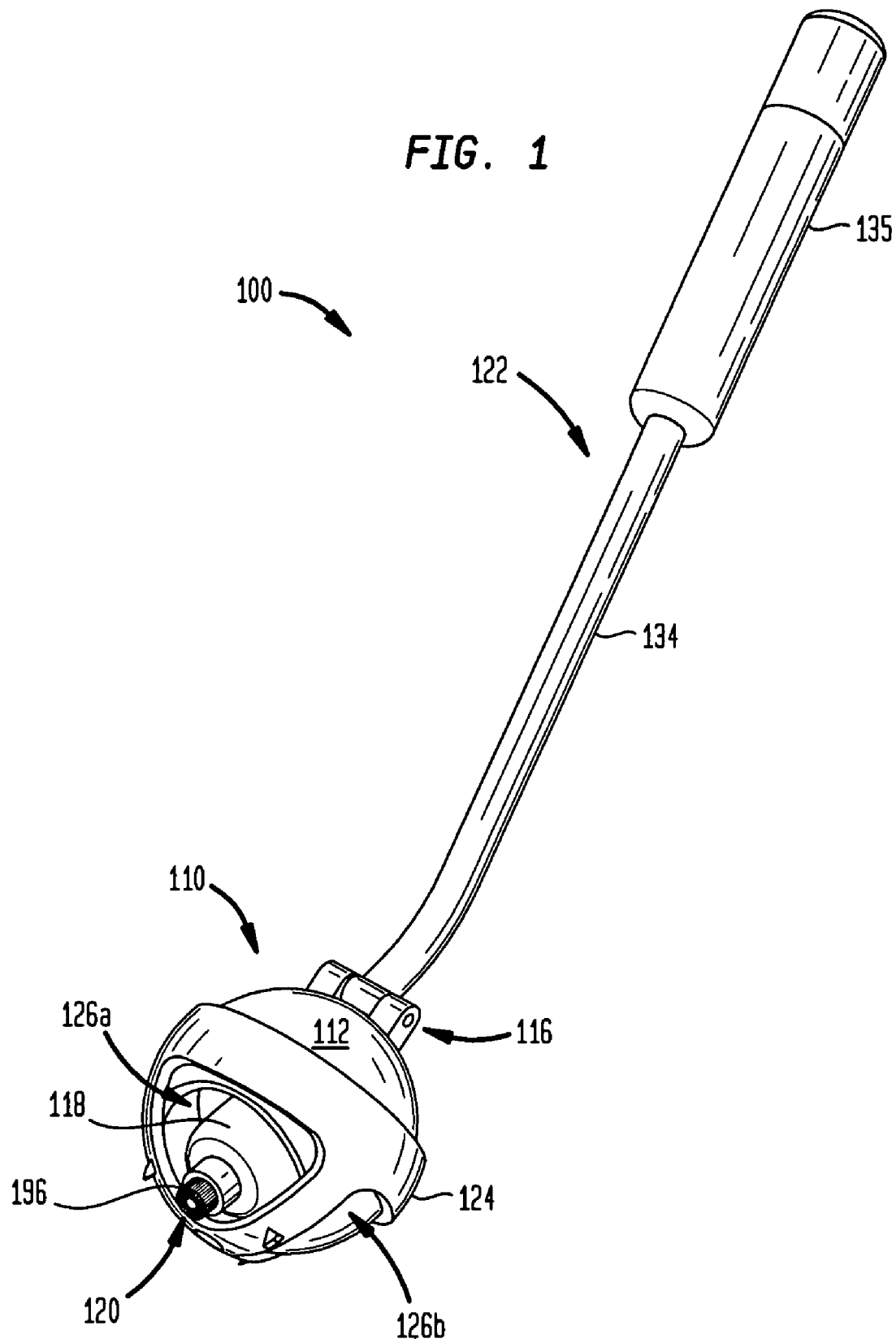
FIG. 1 is a perspective view of a bone-reaming system in accordance with a first embodiment of the present invention.

Referring to the drawings wherein like reference numerals refer to like elements, there is shown in FIG. 1, in accordance with a first embodiment of the present invention, a bone-reaming system 100 which includes a cutting apparatus 110, a routing guide 124, and a handle 122. Cutting apparatus 110 preferably fits within routing guide 124 and is pivotally connected to handle 122 through a connection 116, shown more clearly in FIGS. 2 through 4. Routing guide 124 is preferably configured to fit within a socket or other cavity portion of a ball and socket joint, such as the acetabulum of the hip. Cutting apparatus 110 may be inserted into routing guide 124 whereby its position and orientation may be manipulated through the use of handle 122. Prior to a surgical procedure, routing guide 124 may be manufactured or configured to include one or more cutouts (shown in FIGS. 1, 3 and 4 as cutouts 126a-c) of any predefined size and shape, such that each may allow cutting apparatus 110 to cut the corresponding adjacent portions of a bone cavity. When routing guide 124 is anchored to a bone cavity, such as the acetabulum, only those predefined portions of bone which are adjacent to the cutouts 126 are exposed. The resulting procedure thusly allows less opportunity for unnecessary bone cutting because routing guide 124 is positioned to protect the portions of the bone which are to remain uncut.

Figure 2:
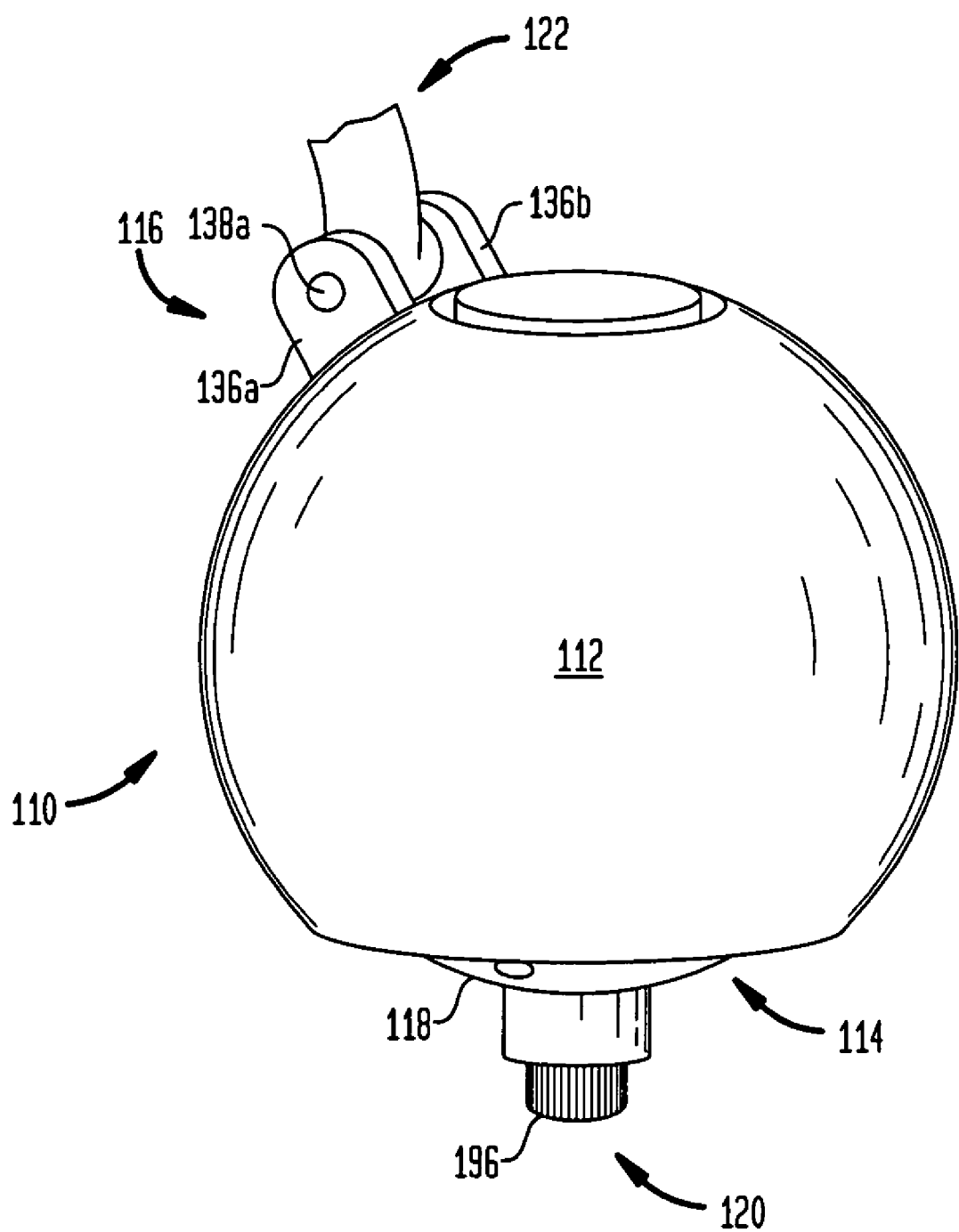
FIG. 2 a perspective view of a cutting apparatus in accordance with the system of FIG. 1.
Figure 3:
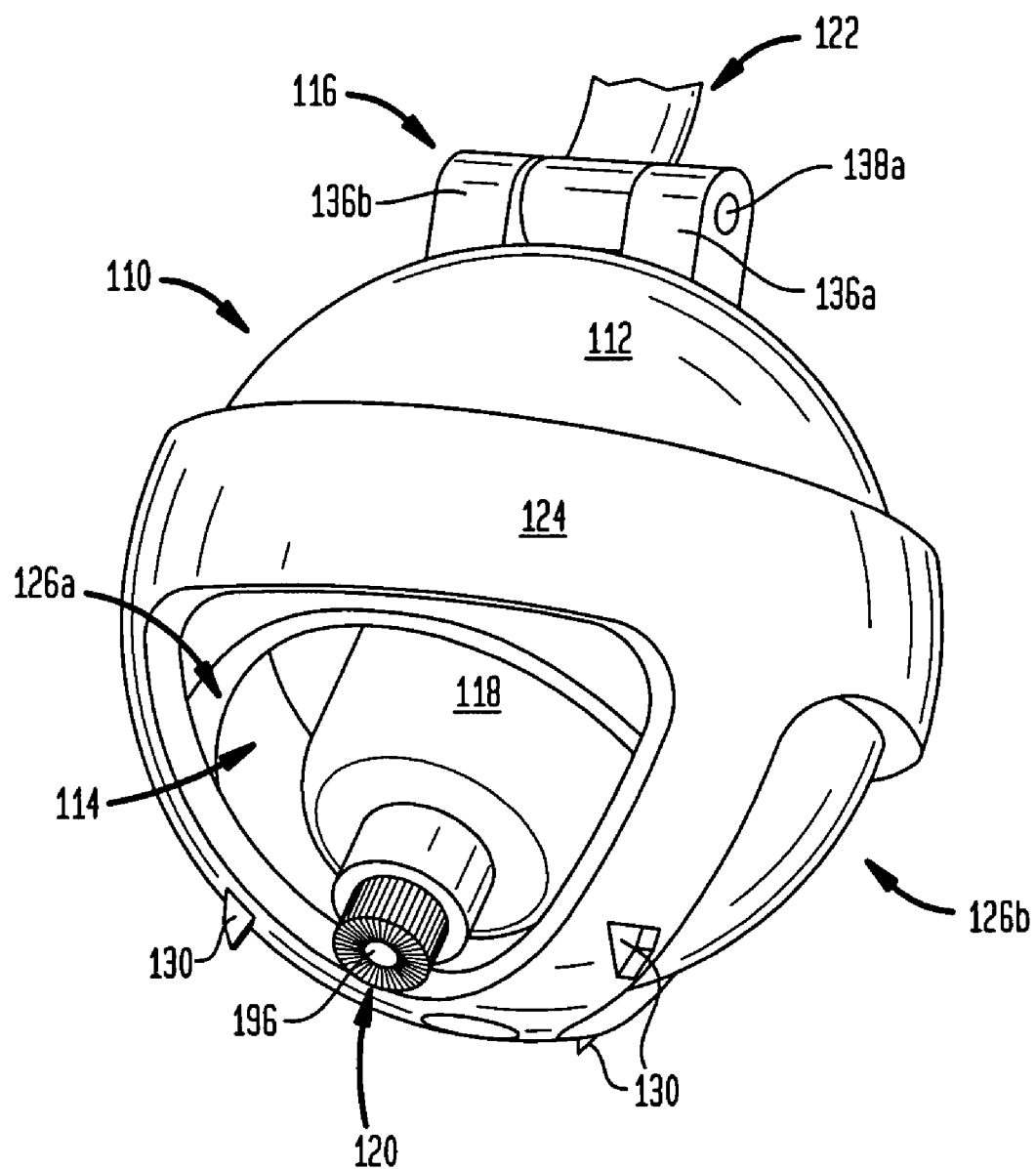
FIG. 3 is a perspective view of a cutting apparatus disposed within a routing guide in accordance with the system of FIG. 1.
Figure 4:
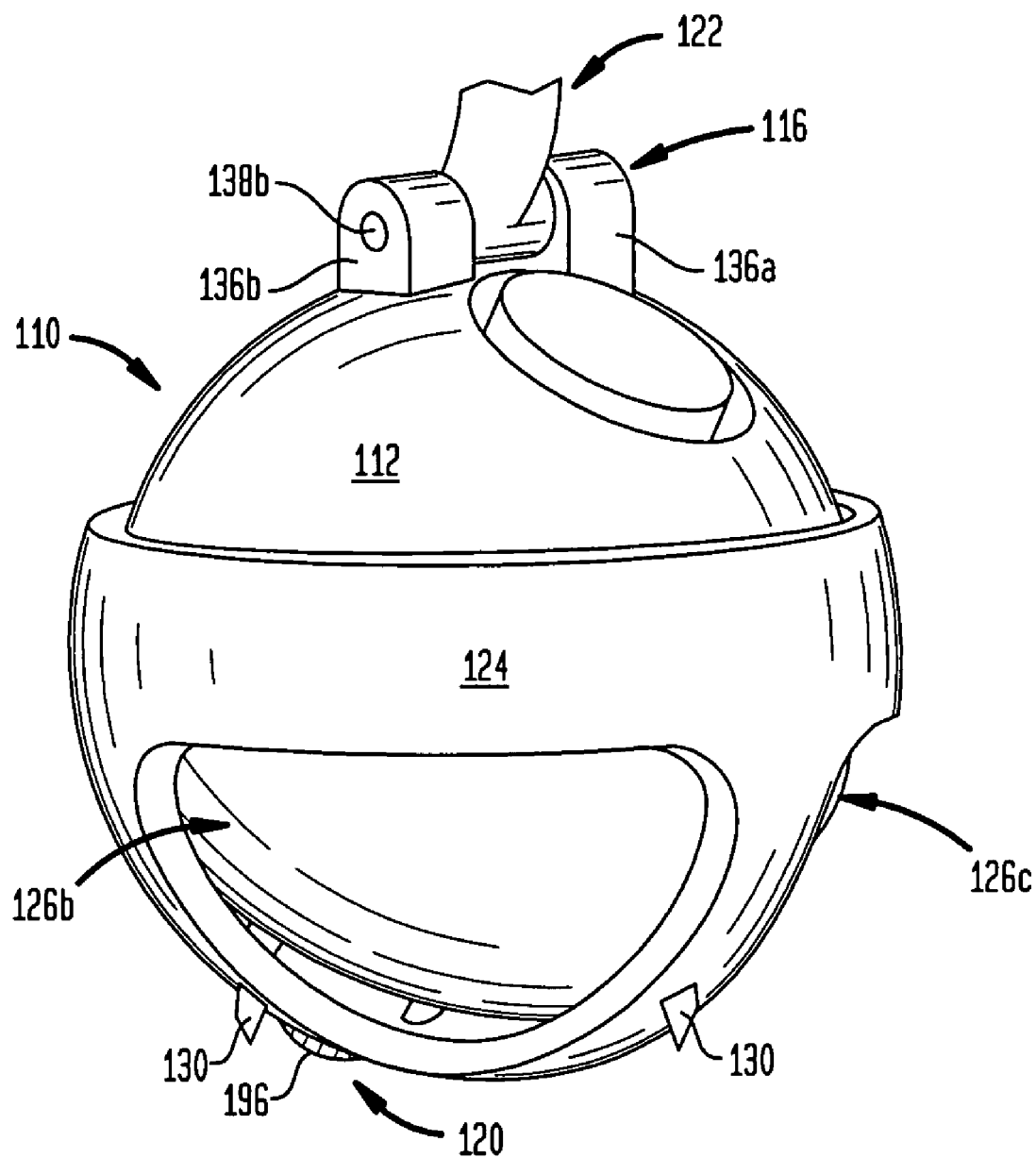
FIG. 4 is another perspective view of the cutting apparatus and routing guide of the system of FIG. 1.

In accordance with the first embodiment, cutting apparatus 110 is more clearly shown in FIGS. 2 through 4. Cutting apparatus 110 includes a housing 112, a connection 116, an electric motor 118, and a cutter 120. As the outermost surface of cutting apparatus 110, housing 112 is preferably shaped to be articulable with a bone cavity. Housing 112, which encloses motor 118 includes an aperture 114, through which cutter 120 protrudes, is preferably spherical, though other configurations are contemplated and would not alter the operability of cutting apparatus 110. The small size and mobility of cutting apparatus 110 is due in large part to motor 118, which is disposed within housing 112; therefore, there is no need to translate motion to cutting apparatus 110 from a source external to the patient's body. One suitable motor 118 for use in connection with the present invention is a 15 Watt VDC Maxon Pancake Motor with a sensorless driver. Other suitable motors would be apparent to those of ordinary skill in the art. Motor 118 preferably receives power from an outside source and creates its own motion that it supplies to cutter 120. Such a translation of motion is independent of the orientation of cutting apparatus 110 within the bone cavity. The disposition of motor 118 also increases the range of motion of cutting apparatus 110. The configuration of motor 118 replaces a more invasive structure through which a motor, such as a drill, would be disposed outside of the patient's body, where one or more axes would be necessary to provide motion from the motor to a cutting device. In accordance with the first embodiment, motor 118 may be rigidly connected to housing 112 through any means well known in the art, such as through the use of screws, welding, and/or adhesive. Cutter 120 is connected to motor 118 and includes a burr 196, which is connected to motor 118 in preferably an axial manner. Burr 196 is positioned through aperture 114 to engage a bone surface when housing 112 articulates within a bone cavity. Connection 116 is disposed on housing 112 and connects handle 122 to cutting apparatus 110. Connection 116 is preferably pivotable and comprised of first flange 136a and second flange 136b, each having a respective pin hole 138a and 138b which are preferably coaxial. Such a configuration allows handle 122 to be disposed between flanges 136 and secured by inserting a pin 144 (not shown) through pin holes 138 and handle 122.

In addition to the spherical shape of housing 112 of the first embodiment, alternate configurations may allow for the same operation of cutting apparatus 110. For example, housing 112 may be cubic with the corners of its faces positionable within routing guide 124. Housing 112 may alternatively be star shaped, where its points define an outer surface that contacts routing guide 124. The shape of a circular band is also contemplated where motor 118 and cutter 120 are more exposed with respect to the interior of routing guide 124. The shape and configuration of housing 112 is only limited by the dimensions of routing guide 124, which must alternately be dimensioned to fit within the bone cavity. Therefore, housing 112 may be a cube, a rectangular prism, a triangular prism, a cylinder, or any other known or arbitrary shape, with the only structural requirements of housing 112 being that it fit within and be moveable within routing guide 124 and the bone cavity with which cutting apparatus 110 is designed to articulate.

In accordance with the first embodiment, both motor 118 and cutter 120 are preferably positionable both within housing 112 and also with respect to each other which allows the user to set the cutting depth by setting the distance from which cutter 120 protrudes from housing 112. Each section of bone may be cut to a predetermined depth that is different from each other section. Through the use of electronic manipulation, it may be possible for cutter 120 to be moved in an inward and/or outward direction relative to motor 118 during use. However, this may only be possible if housing 112 is of a sufficient size to allow such movement therein. This may increase the range of motion of cutter 120 during operation. Cutter 120, which incorporates burr 196 in the first embodiment, may alternately include any type of cutting device used for cutting bone, such as one or more blades, a helix-shaped cutter, a laterally-moving cutter, or a scoop-shaped device. Burr 196 may be replaceable to accommodate larger, smaller, or arbitrarily shaped cutting procedures.

Alternate configurations of connection 116 are adaptable without compromising the operability of the bone-reaming system 100. For example, connection 116 may be constructed so as to allow handle 122 to pivot with respect to cutting apparatus 110 in more than one degree of freedom. Those of ordinary skill in the art would readily recognize configurations that could be employed to achieve this type of moveability. For example, a simple ball and cavity configuration could be included in lieu of connection 116 shown in the Figures.

Routing guide 124, as shown in FIGS. 1, 3, and 4 in accordance with the first embodiment, preferably includes a first cutout 126a, a second cutout 126b, a third cutout 126c, and three spikes 130. First cutout 126a, second cutout 126b, and third cutout 126c are each of generally triangular shape, though in theory any shape may be appropriate for any procedure. In fact, the number of cutouts and their respective shapes may be predetermined based on individual surgical need and may be dictated by the shape of the defect being repaired. Routing guide 124 may also be standardized for certain procedures which require identically configured cutouts. The only limitation on the size and shape of the cutouts is that they must accommodate burr 196. Of course, differently sized and shaped burrs could also be employed when smaller and/or larger areas are to be repaired. Any number of cutouts is possible and contemplated.

Predefining which portions of the cavity must be cut allows for routing guide 124 to be fabricated to the exact specifications of each surgical procedure. When removably implanted in the cavity, routing guide 124 then minimizes the risk of error during the procedure by covering the portion of the bone cavity meant to remain uncut, and uncovering the portion to be cut. Not only does bone-reaming system 100 reduce the possibility of error, it also allows for a user with less skill or experience than an expert in the field to successfully perform an operation, even though such a person is not likely to perform surgery.

In FIGS. 3 and 4, cutting apparatus 110 is shown disposed within routing guide 124, allowing burr 196 to extend through first cutout 126a. The boundaries of first cutout 126a, second cutout 126b, and third cutout 126c define the only portion of the bone reachable by burr 196. As such, when routing guide 124 is manufactured and anchored to the proper surgical specifications, cutting apparatus 110 may be maneuvered without the danger of mistakenly cutting the wrong portion of the bone. Routing guide 124 thus acts as both a guide and a safety net allowing the user to manipulate cutting apparatus 110 according to "feel" rather than "sight" when burr 196 is disposed within the bone cavity, the surface of which may be out of the user's view.

In accordance with the first embodiment, routing guide 124 has three spikes 130 that are anchored into the adjacent bone surface of the bone cavity to anchor routing guide 124. Holes may be tapped or drilled into the bone surface, e.g., the acetabulum, prior to surgery for guiding the spikes and thereby providing for a more precise placement of routing guide 124. Additional anchoring such as cement or other adhesive compound may be desired to keep routing guide 124 secured within the cavity. However, it is typically the aim that such guide be removed prior to the completion of the surgical procedure.

In accordance with the first embodiment, FIG. 1 shows handle 122 which is comprised of a stem 134 and a grip 135. Handle 122 is pivotally connected to cutting apparatus 110 which is provided with great freedom to articulate because handle 122 can remain in substantially the same position outside the patient's body while allowing cutting apparatus 110 to assume any orientation necessary to cut the adjacent bone surface. Though handle 122 and connection 116 have been described so that handle 122 may be detachably connected to housing 112, handle 122 may alternatively be integrally connected thereto. If handle 122 is rigidly connected to housing 112, stem 134 may be bendable and/or lockable so that it does not become an obstacle to the surgical procedure.

Bone-reaming system 100 preferably allows the user to control cutting apparatus 110 with handle 122 from outside the patient's body. This results in a less invasive surgical procedure by reducing the size and amount of instrumentation and material that must be introduced into the body during the procedure. Moreover, a ball and socket joint need only be separated enough to allow insertion of routing guide 124 and cutting apparatus 110, at which point the bone cavity may be cut via manipulation of handle 122. This may reduce the separation between the bone socket and mating ball that is necessary to allow the user full access to the bone cavity for proper and precise operation. Because handle 122 may pivot with respect to cutting apparatus 110, the procedure may also be less invasive because cutting apparatus 110 may articulate with the bone cavity without requiring the area adjacent to the bone cavity, where the mating ball is usually disposed, to remain clear in order to accommodate for the movement of a rigidly attached handle. Such a rigid fixation of handle 122 to the surface of cutting apparatus 110 may require greater separation of the joint to keep the adjacent space clear. Nonetheless, such a construction is clearly contemplated in relation to the present invention.

Figure 5:
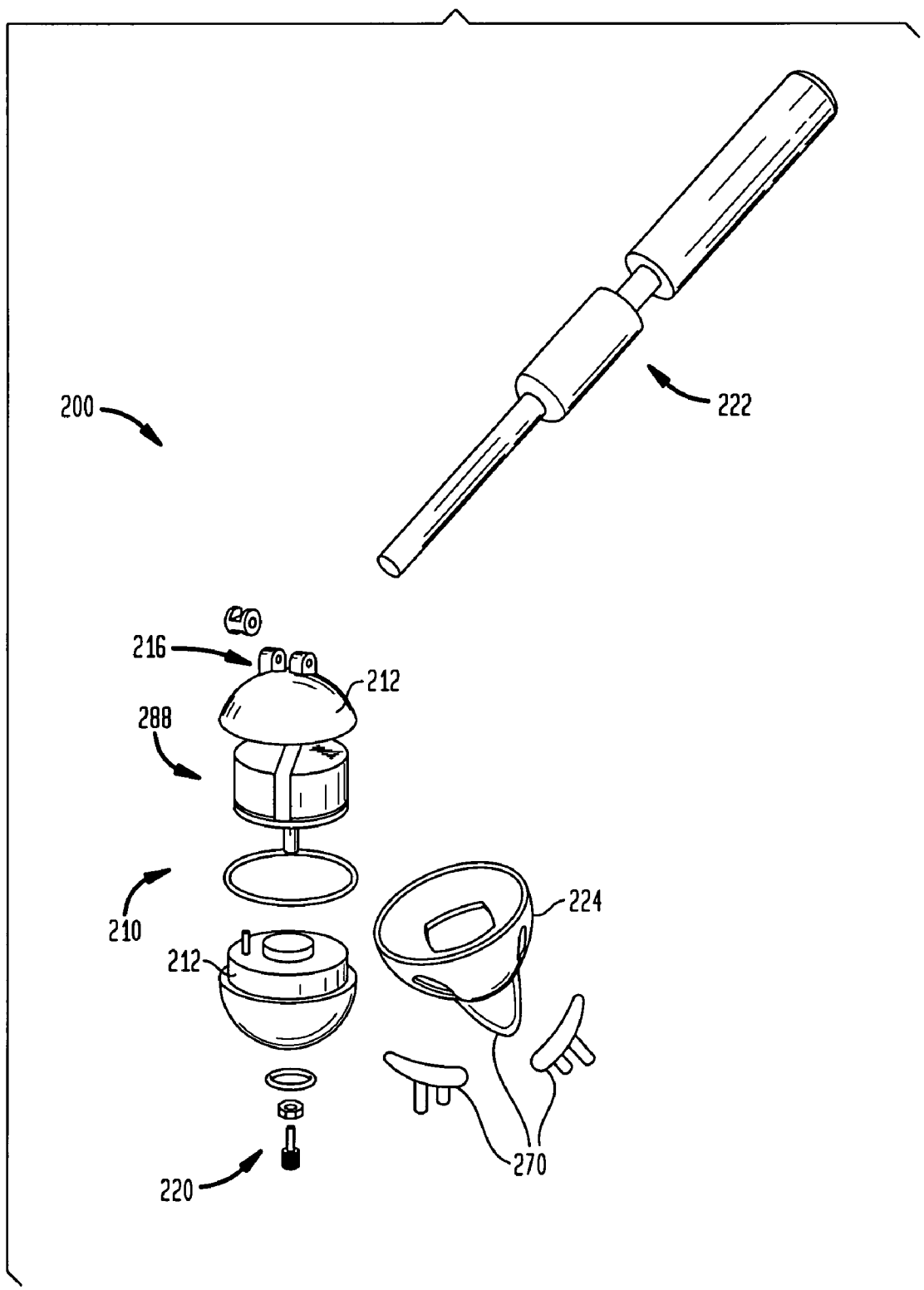
FIG. 5 is an exploded view of a bone-reaming system in accordance with a second embodiment of the present invention.

There is shown in FIG. 5, in accordance with a second embodiment of the present invention, an exploded view of a bone-reaming system 200 which includes a cutting apparatus 210, a routing guide 224, and a handle 222. Cutting apparatus 210 is also shown in exploded view, where a housing 212 encloses a driving assembly 288 that drives a cutter 220. Proximate to routing guide 224 are three inserts 270 which may be implanted into the cut portions of the bone cavity. Handle 222, depicted in an exploded view, is preferably connected to cutting apparatus 210 at a connection 216. This allows for manipulation of cutting apparatus 210 through handle 222 while handle 222 is disposed outside of the patient's body.

Figure 6:
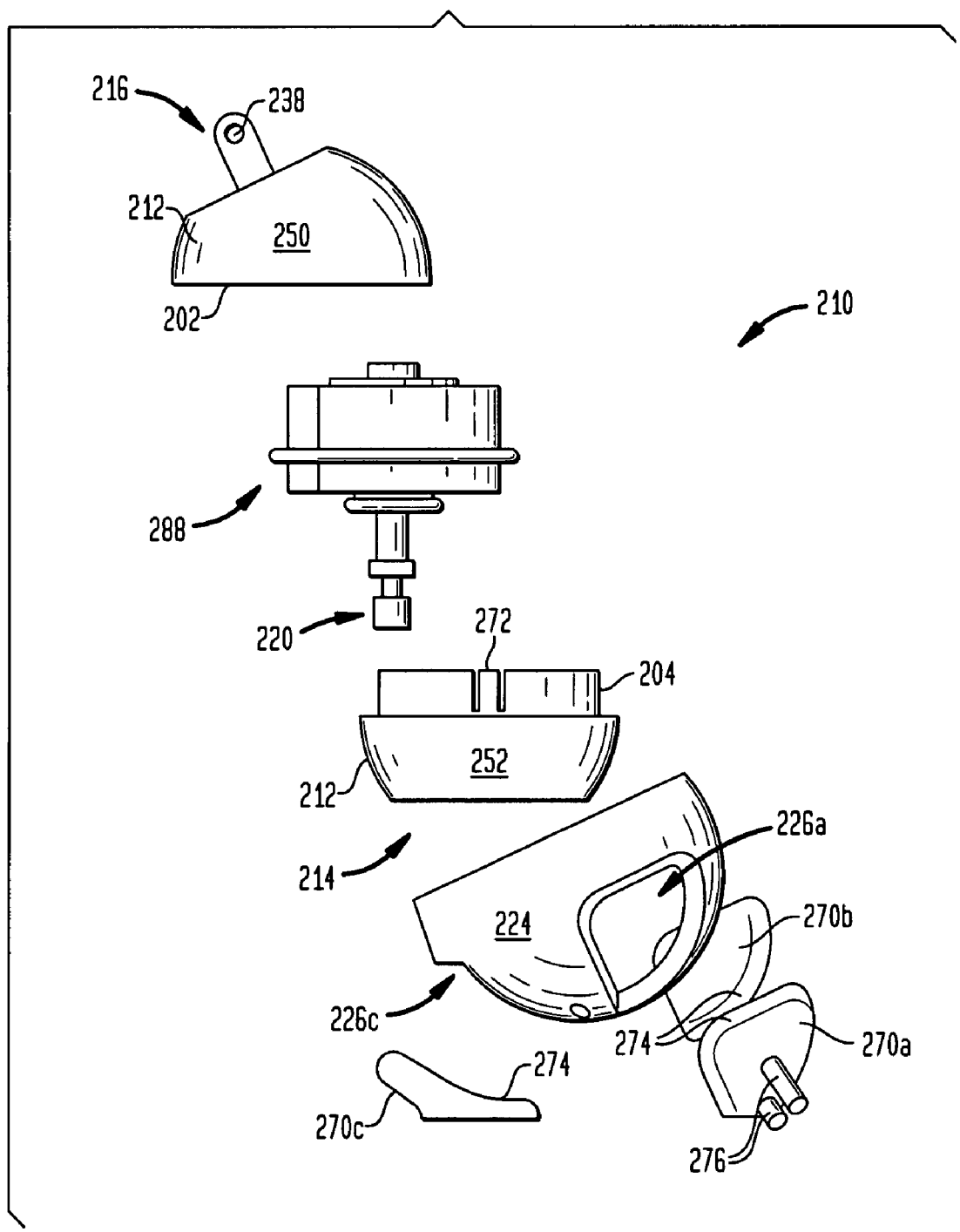
FIG. 6 is an exploded view of a cutting apparatus and a routing guide in accordance with the system of FIG. 5.

Cutting apparatus 210 in accordance with the second embodiment is more clearly shown in an exploded view in FIG. 6. A top 250 and a bottom 252 are both preferably substantially hemispherical and together comprise housing 212 within which is disposed driving assembly 288, better shown in FIG. 7. Bottom 252 includes an aperture 214, a wall 204, and a snap lock 272, a preferred means through which it attaches to top 250. Wall 204 is preferably substantially circular, and of a diameter that is less than that of a rim 202 of top 250, whereby housing 212 is "closed" when wall 204 is disposed inside rim 202. Snap lock 272 is preferably received within rim 202 of top 250 to secure the closure of housing 212. Preferably, snap lock 272 is designed to deflect enough to engage rim 202 of top 250, and thereafter spring back into position, thereby locking top 250 and bottom 252 together. Of course, other locking devices or structure may be employed to form this connection.

Routing guide 224 is depicted in the second embodiment of FIG. 6 having a first cutout 226a, a second cutout 226b (not shown), and a third cutout 226c. A first insert 270a, a second insert 270b, and a third insert 270c are disposed proximate to their respective cutouts, to which they may also be similarly dimensioned. Each insert 270 preferably has a thickness 274 which is designed to replace the portion of the bone that is removed by cutting apparatus 210. Each insert 270 preferably includes one or more protrusions or keels 276 that are anchored into the bone to aid in securing insert 270 to the bone. After inserts 270 have been implanted into the bone cavity, the result is such that the surface of the bone cavity substantially continuous. It is noted that inserts 270 may be constructed of any suitable biocompatible material, such as ceramic, stainless steel, a polymer or the like. Although inserts 270 are shown in the drawings and discussed above, other suitable implants may be utilized. For example, it is contemplated to provide a material which may be molded into the portions of bone which has been reamed through the use of cutting apparatus 210. Suitable materials may include, without limitation, polyurethane, Delrin, Ultem, PVA, PEEK, and/or polyethylene.

Figure 7:
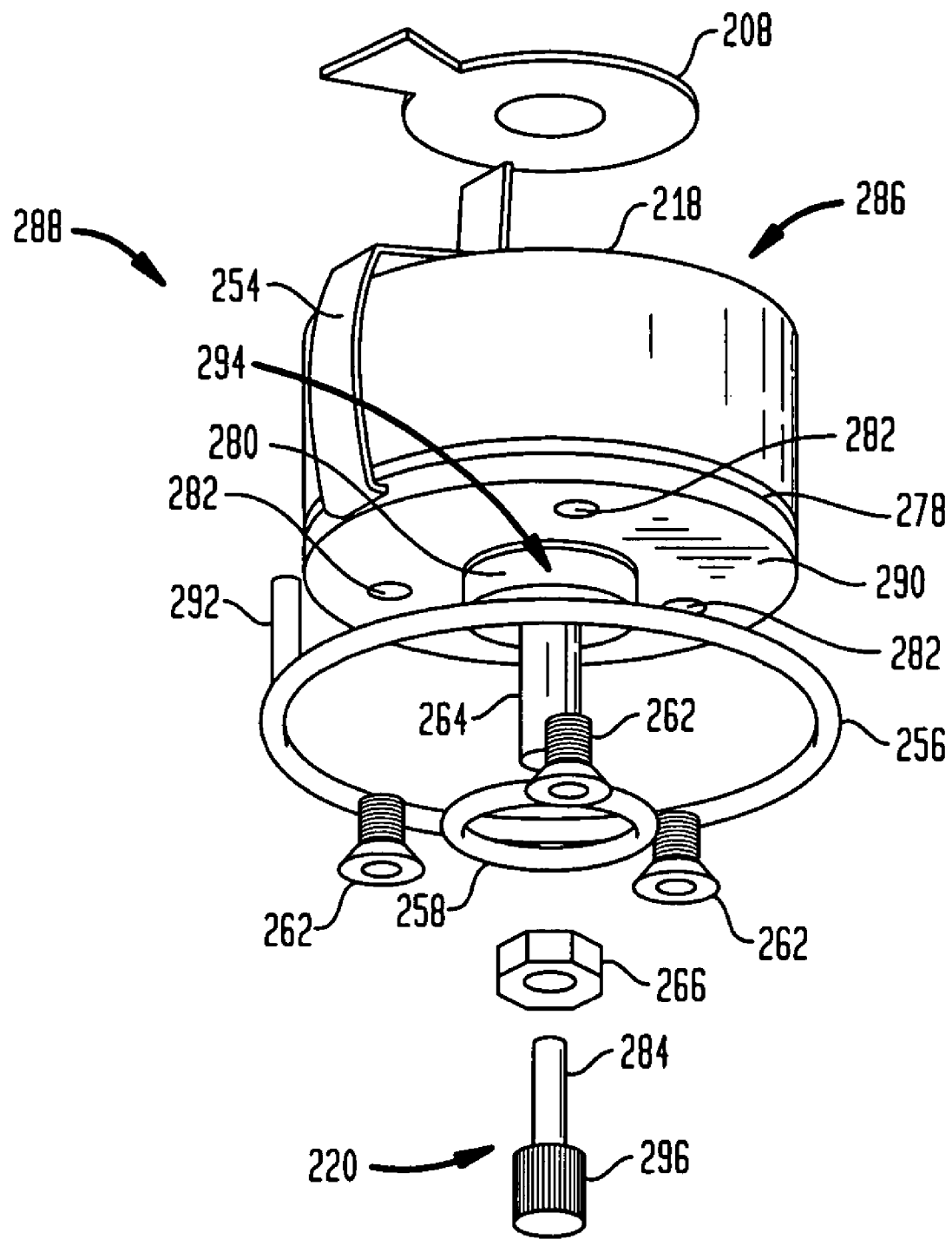
FIG. 7 is an exploded view of a driving assembly in accordance with the system of FIG. 5.

FIG. 7 shows driving assembly 288 in an exploded view in accordance with the second embodiment. Motor 218 includes a top surface 286, a bottom surface 290, a boss 280 that protrudes downward from bottom surface 290, and a recess 278 proximate to bottom surface 290 for receiving a large gasket 256. A conductor 254 is disposed from recess 278 to top portion 286. In the embodiment shown, conductor 254 is a ribbon cable utilized in providing power to the motor 218. A ring 208 is positioned proximate to top portion 286, for keeping conductor 254 away from the rotating portions of the device. A peg 292 is included for preventing a cable or the like from coming into contact with the spinning rotor of the electric motor. Boss 280 includes a groove 294 about which is disposed a small o-ring 258. A drive shaft 264 protrudes from boss 280. A screw 262 may be secured into a screw hole 282 which is positioned on bottom surface 290. According to the second embodiment of FIG. 7, three flat head screws 262 and three screw holes 282 are incorporated for mounting the motor to the housing. A cutter 220 includes burr 296 and a cutting shaft 284 which may be inserted into drive shaft 264. A nut 266 may be securably positioned around drive shaft 264 so as to clamp cutter shaft 284 into drive shaft 264. Cutter 220 is preferably a one piece burr inserted into the hollow drive shaft of the motor 264. Additionally, the hollow shaft itself may be threaded on a taper and slotted. Once the nut is tightened on to the shaft the hollow squeezes down on the cutter 220 and is locked in place.

Figure 8:
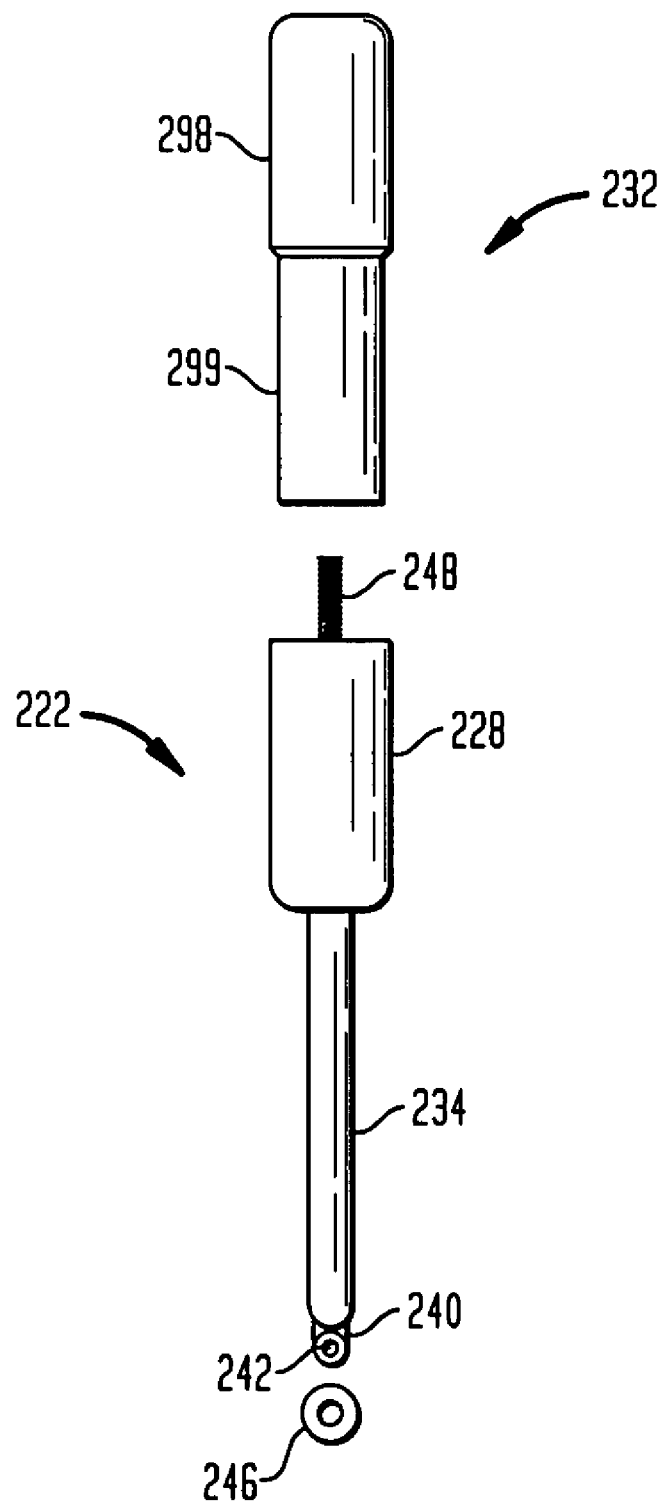
FIG. 8 is an exploded view of a handle in accordance with the system of FIG. 5.

FIG. 8 depicts handle 222 in an exploded view in accordance with the second embodiment of the present invention. As shown, handle 222 is comprised of a lower grip 228, an upper grip 232, a post 248, a stem 234, and a base 240. Upper grip 232 is comprised of a small cylinder 299 rigidly connected to a large cylinder 298. Small cylinder 299 may be slidably connected into lower grip 228. The diameter of small cylinder 299 is preferably less than that of large cylinder 298 so that small cylinder 299 may be slidably received within lower grip 228. Internal to upper grip 232 is threaded post 248 through which upper grip 232 and lower grip 228 are secured. Upper grip 232 and lower grip 228 may collectively include a knurl or a smooth or scored rubber coating so as to improve the user's grip of handle 222. Stem 234 may be straight, curved, or include one or more angled bends. Base 240 connects to the proximate end of stem 234 and includes a through hole 242 which, when handle 222 is attached to housing 212 through connection 216, may be coaxially aligned with pinholes 238 of connection 216, better shown in FIG. 6. A pin 244 (not shown) is inserted through pinholes 238 to pivotally connect handle 222 to connection 216. At least one washer 246 may be disposed between thruhole 242 and pinhole 238.

Figure 9:
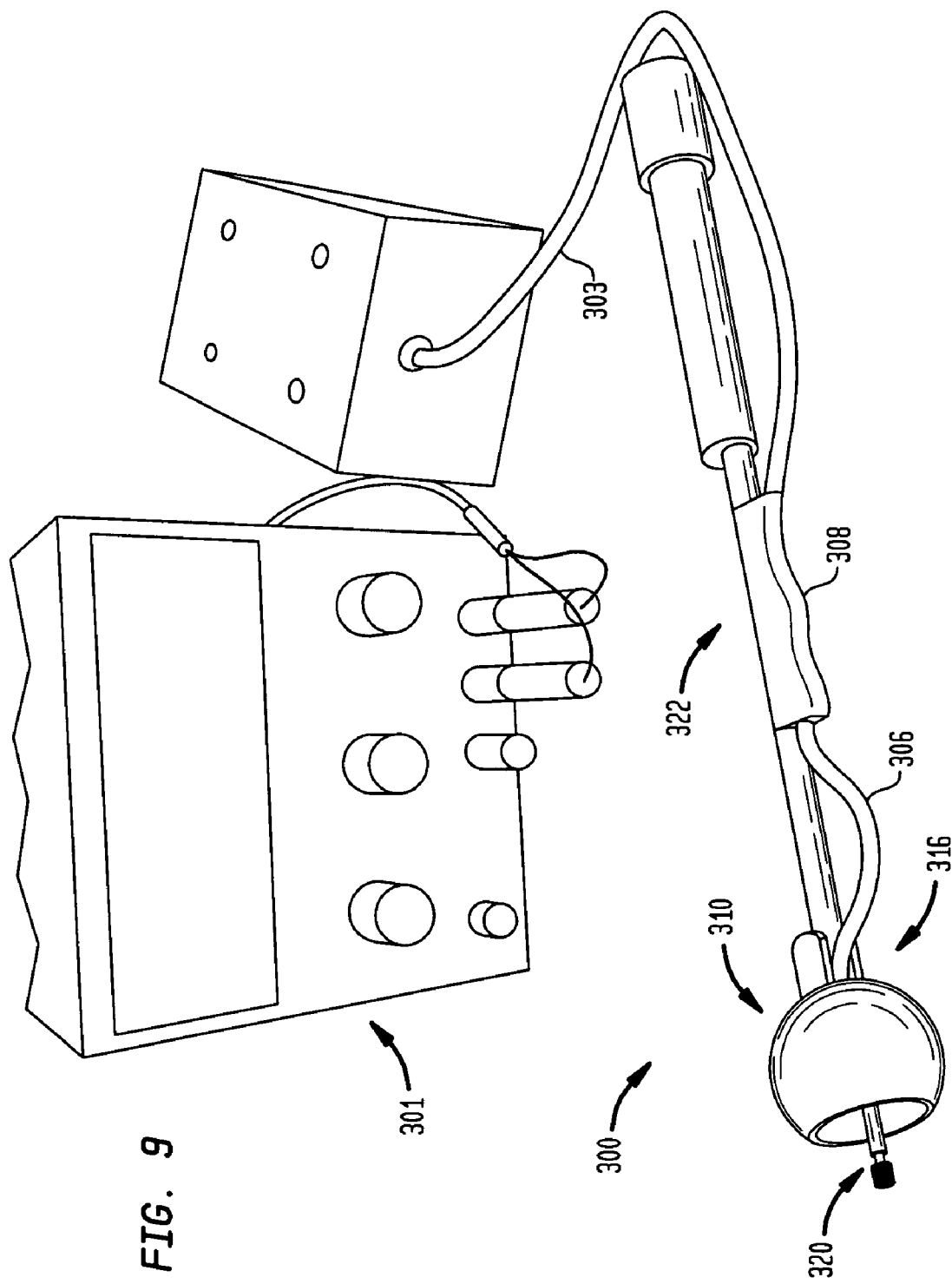
FIG. 9 is an illustration of a bone-reaming system with a power cord and power supply in accordance with a third embodiment of the present invention.
Figure 11:
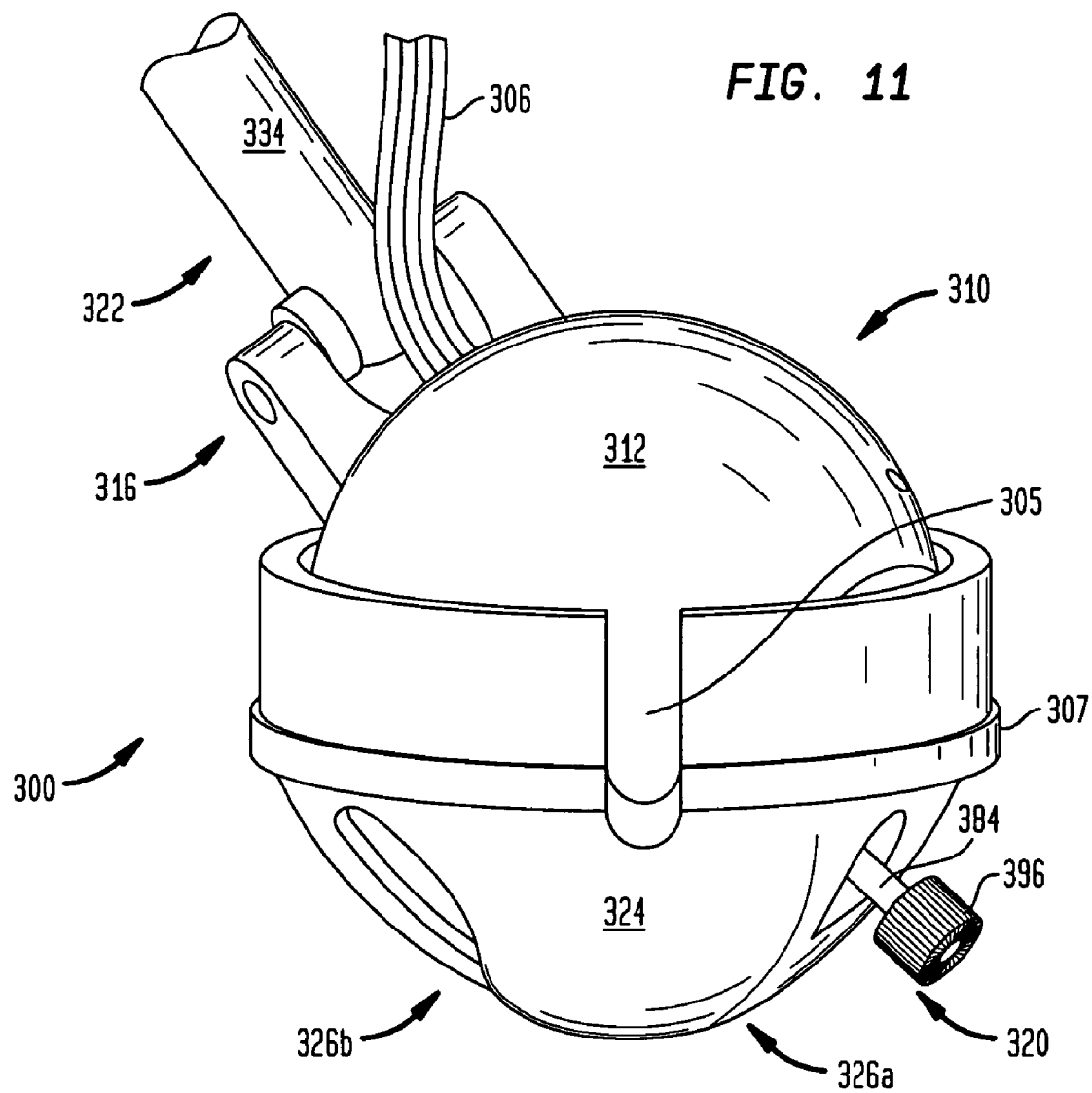
FIG. 11 is a perspective view of a cutting apparatus disposed within a routing guide in accordance with the third embodiment bone-reaming system of FIG. 9.

There is shown in FIG. 9, in accordance with a third embodiment of the present invention, a bone-reaming system 300 that includes a cutting apparatus 310 that is preferably pivotally connected to a handle 322. The main differences between the second and third embodiments of the present invention are the practicality of manufacture of third embodiment device, as well as the inclusion of a radial thrust bearing (not shown) to better handle axial loading on the cutter. Bone-reaming system 300 also includes a routing guide 324 which is shown in FIG. 11. In FIG. 9, cutting apparatus 310 is shown connected to a power supply 301 through a ribbon 306 and a power cord 303. It is to be understood that power supply 301 may be any power supply suitable to provide sufficient power to the motor of system 300. A flexible connection like ribbon 306 is preferred as it allows power supply 301 to supply cutting apparatus 310 with power while remaining outside of the patient's body. It is also contemplated to include a power source within cutting apparatus 310, in any of the embodiments disclosed in the present invention. Of course, such a power source would need to be sized and shaped accordingly. For example, a battery or series of batteries could be housed in the handle of any of the above-described bone-reaming systems.

Figure 10:
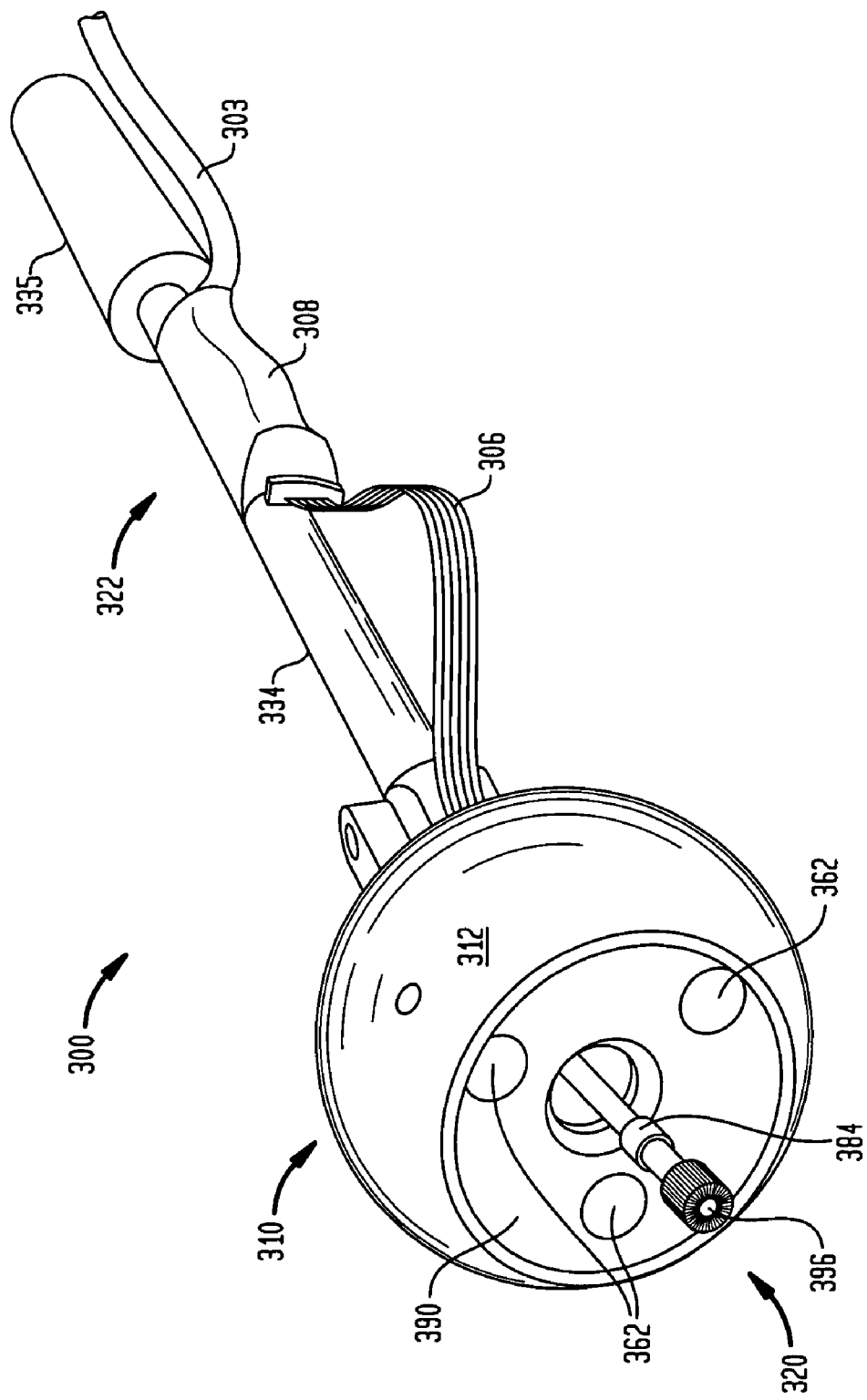
FIG. 10 is a perspective view of the bone-reaming system of FIG. 9.

In accordance with the third embodiment, FIG. 10 depicts bone-reaming system 300 where cutting apparatus 310 and handle 322 are more clearly shown. Cutting apparatus 310 includes a housing 312 that is disposed about a motor (not shown), of which a bottom surface 390 of housing 312 is shown. Three screws 362 are disposed within three adjacent screw holes 382 in bottom surface 390 in order to mount surface 390 to the motor thereto. Handle 322 includes a stem 334 and a grip 335. Ribbon 306 extends from cutting apparatus 310 and connects to a power cord 303 through a power connection 308, which is preferably taped to handle 322 to avoid interfering with the operation of bone-reaming system 300. Ribbon 306 extends through connection 316 and may be comprised of any appropriate electrical connection device, through which a power supply 301 (shown in FIG. 9) may be connected to motor 318. Ribbon 306 is preferably flexible so as not to impede the movement of cutting apparatus 310 within routing guide 324.

FIG. 11 shows cutting apparatus 310 disposed within routing guide 324 in accordance with the third embodiment. Routing guide 324 includes a first cutout 326a and a second cutout 326b, with a cutter 320 of cutting apparatus 310 protruding through first cutout 326a. Routing guide 324 is shown having a slot 305 and a lip 307.

Figure 12:
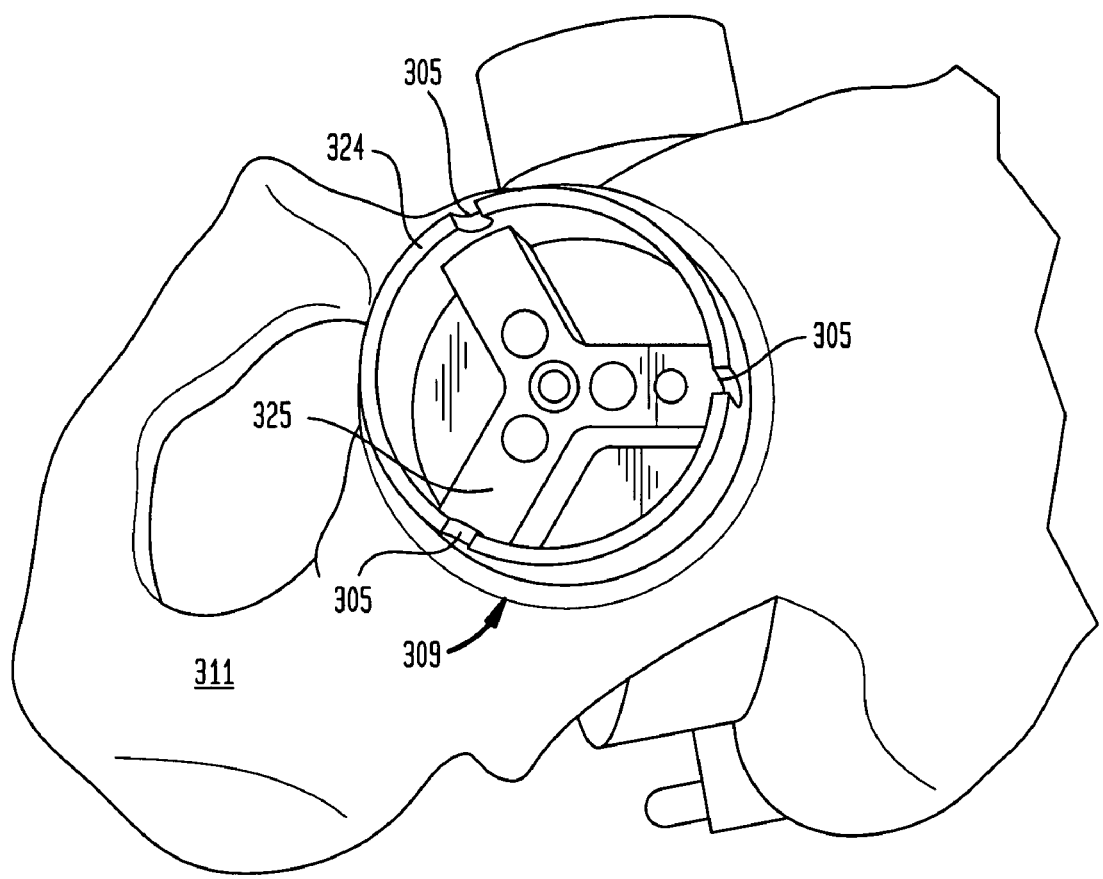
FIG. 12 is an illustration of a routing guide disposed within a bone cavity in accordance with the third embodiment bone-reaming system of FIG. 9.

FIGS. 12 through 17 illustrate one exemplary method of using bone-reaming system 300 of the third embodiment of the present invention. FIG. 12 depicts routing guide 324 disposed within bone cavity 309 of bone 311. Routing guide 324 is first removably secured to bone cavity 309 in any way that allows routing guide 324 to remain stable throughout the procedure. If a bonding agent is strong enough to appropriately anchor routing guide 324, it may be used on its own. Any means used to secure routing guide 324 must allow for the removal of itself and routing guide 324 after operation is complete. A drill guide 325 is shown disposed within guide 324 in FIG. 12. Such drill guide 325 is preferably utilized to insert one or more screws or other fixation means through guide 324 and into the bone, so as to fixably attach guide 324 thereto. Of course, such means should be designed for removal prior to the milling or reaming steps of the surgical procedure.

Figure 13:
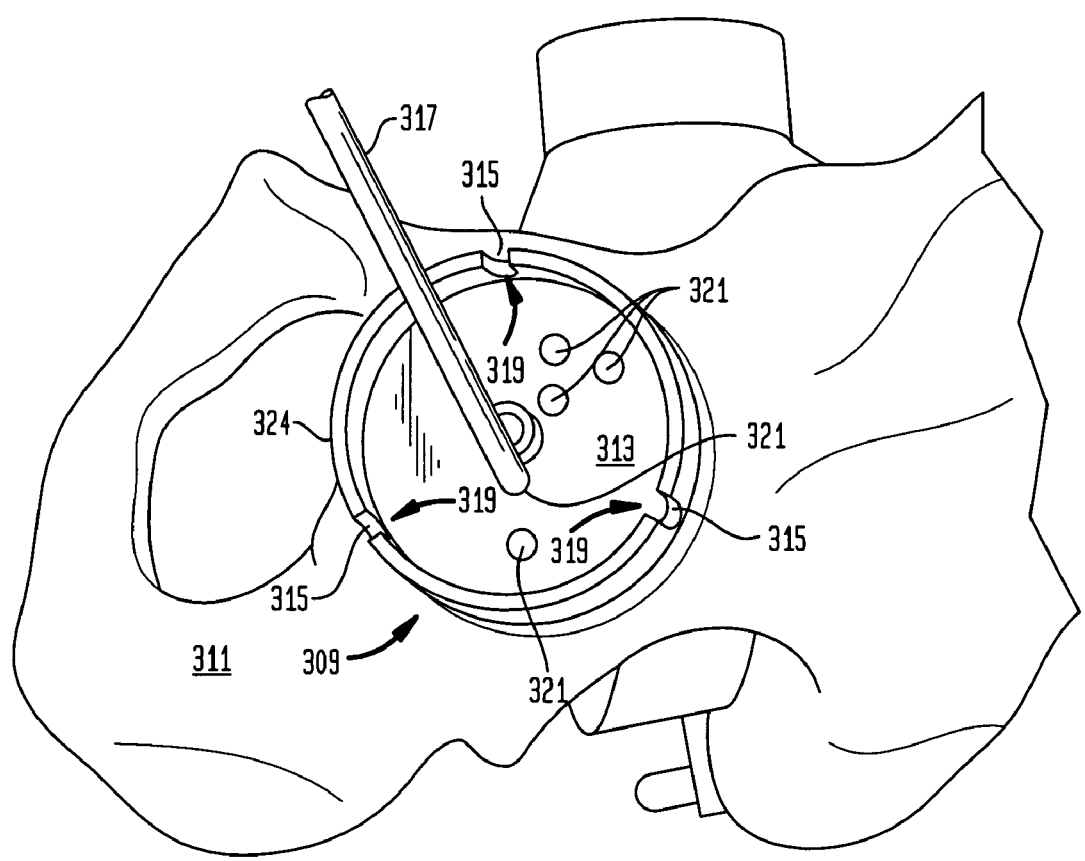
FIG. 13 is an illustration of a drilling procedure in accordance with the third embodiment bone-reaming system of FIG. 9.

FIG. 13 shows another drill guide 313 disposed within routing guide 324 which is removably secured to routing guide 324 to provide a substantially rigid device through which a drill bit 317 is guided into bone cavity 309. As shown in FIGS. 12 and 13, three slots 315 are disposed routing guide 324 which aid in the positioning of drill guide 313. Three tabs 319 along the circumference of drill guide 313 mate with slots 315 when drill guide 313 is inserted to prevent drill guide 313 from moving rotationally as drill bit 317 operates on bone cavity 309. Drill guide 313 includes one or more guide holes 321 through which drill bit 317 is then disposed whereby holes are cut for protrusions 376 of inserts 370. Once drill guide 313 is removably secured to routing guide 324, drill bit 317 may be passed through each guide hole 321 to bore a peg hole 323 in the adjacent portion of bone. Peg holes 323 may be drilled through as many guide holes 321 as necessary in order to provide enough peg holes 323 to anchor the protrusions 376 of inserts 370, which are inserted after the bone reaming is completed. It is noted that this drilling of peg holes 323 for protrusions 376 of inserts 370 may also be performed subsequent to the reaming of areas, as will be discussed more fully below.

Figure 14:
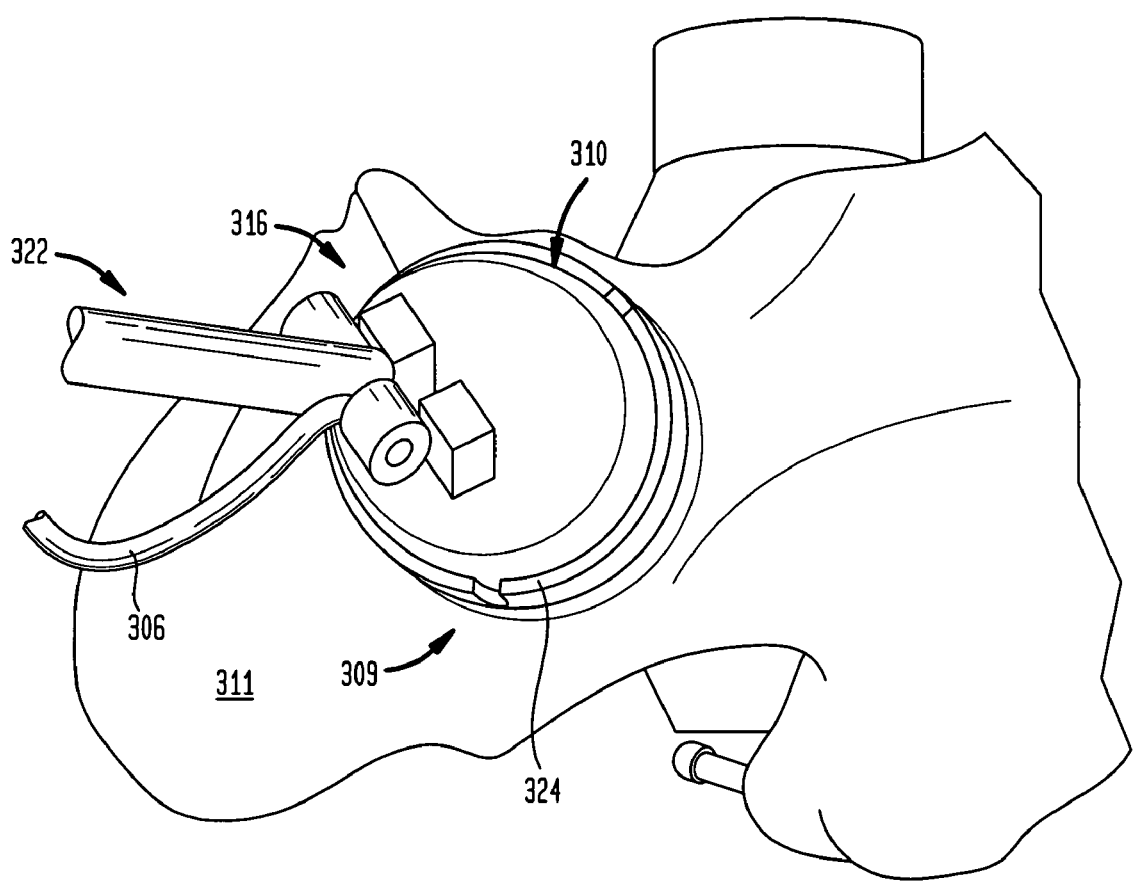
FIG. 14 is an illustration of a bone-reaming apparatus operating in accordance with the third embodiment bone-reaming system of FIG. 9.
Figure 15:
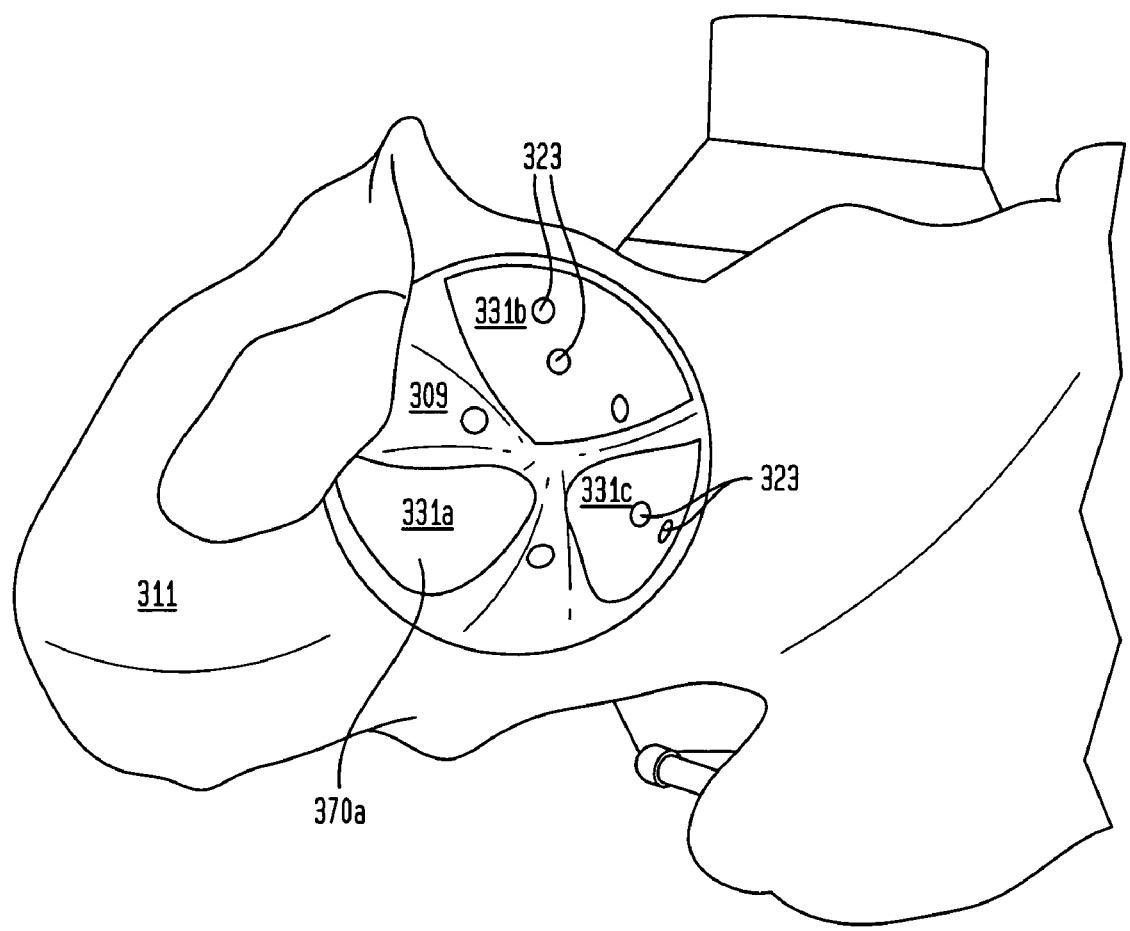
FIG. 15 is an illustration of a reamed bone cavity resulting from the use of the third embodiment bone-reaming system of FIG. 9.

After routing guide 324 is secured, bone cavity 309 may be cut as shown in FIG. 14. Cutting apparatus 310 is disposed within routing guide 324 and rotated through manipulation of handle 22 whereby the portions of bone adjacent to cutouts 326 are cut. A first cutout 326 thus serves as a guide to the user to easily focus burr 396 on the selected portion of the bone cavity to be cut, though it may not be easily seen. By simply manipulating handle 322 to move cutting apparatus 310 out of routing guide 324, housing 312 may be reoriented so that cutter 320 is thereafter disposed within another cutout 326. Therefore, after the portion of bone adjacent to a first cutout 326 has been cut, the portion of bone adjacent to a second cutout 326 may be cut in a similar fashion. This may be repeated for as many times as there are cutouts in routing guide 324. Throughout the procedure, ribbon 306 maintains a supply of power to motor 318 while remaining flexible as handle 322 pivots at connection 316.

After bone cavity 309 is cut, cutting apparatus 310 and routing guide 324 are both removed. Bone cavity 309 may thus appear as in FIG. 15. First insert 370a is placed within a first recess 331a where protrusions 376 are inserted into corresponding peg holes 323. A second recess 331b and a third recess 331c are also mated with corresponding inserts 370. A bonding agent, such as cement or an equivalent adhesive, may be used to further secure insert 370 to the bone cavity. Such a bonding agent may be applied to one or more protrusions 376 and/or to the bone-contacting surface of insert 370 before the insertion thereof.

Figure 16:
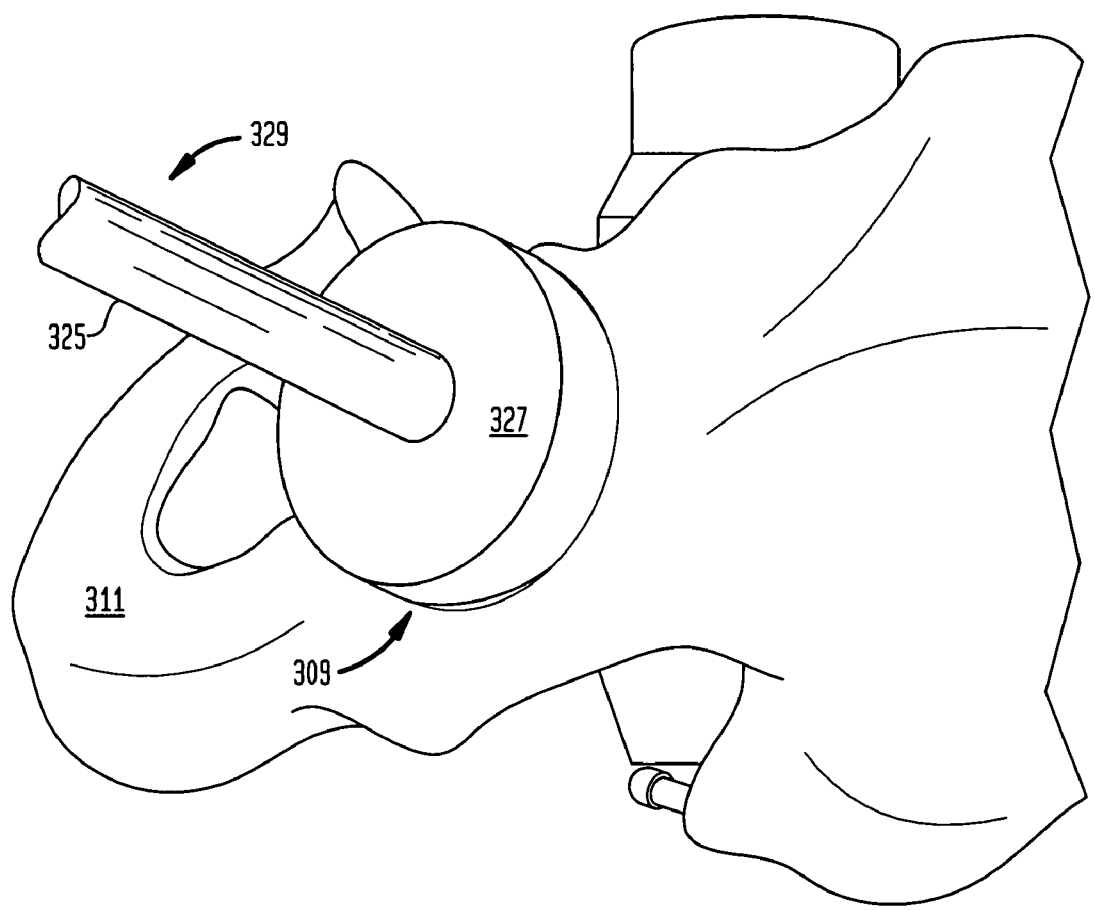
FIG. 16 is an illustration of an impaction device in accordance with the third embodiment bone-reaming system of FIG. 9.

FIG. 16 illustrates the use of an impact device 534 within bone cavity 309 to impactably secure inserts 370. An impact head 532 is manipulated through an impact shaft 530 for temporarily mating impact head 532 and bone cavity 309 to ensure inserts 370 have formed a proper fit with bone cavity 309. Impact head 532 is preferably sized to compliment a generic bone cavity, though any orientation that effectively secures one or more inserts may be appropriate. Once inserts 370 have been inserted into cut recesses 331, impact device 329 is used in either a pressing and/or tamping motion to press fit inserts 370 whereby a substantially continuous bone surface is achieved.

Figure 17:
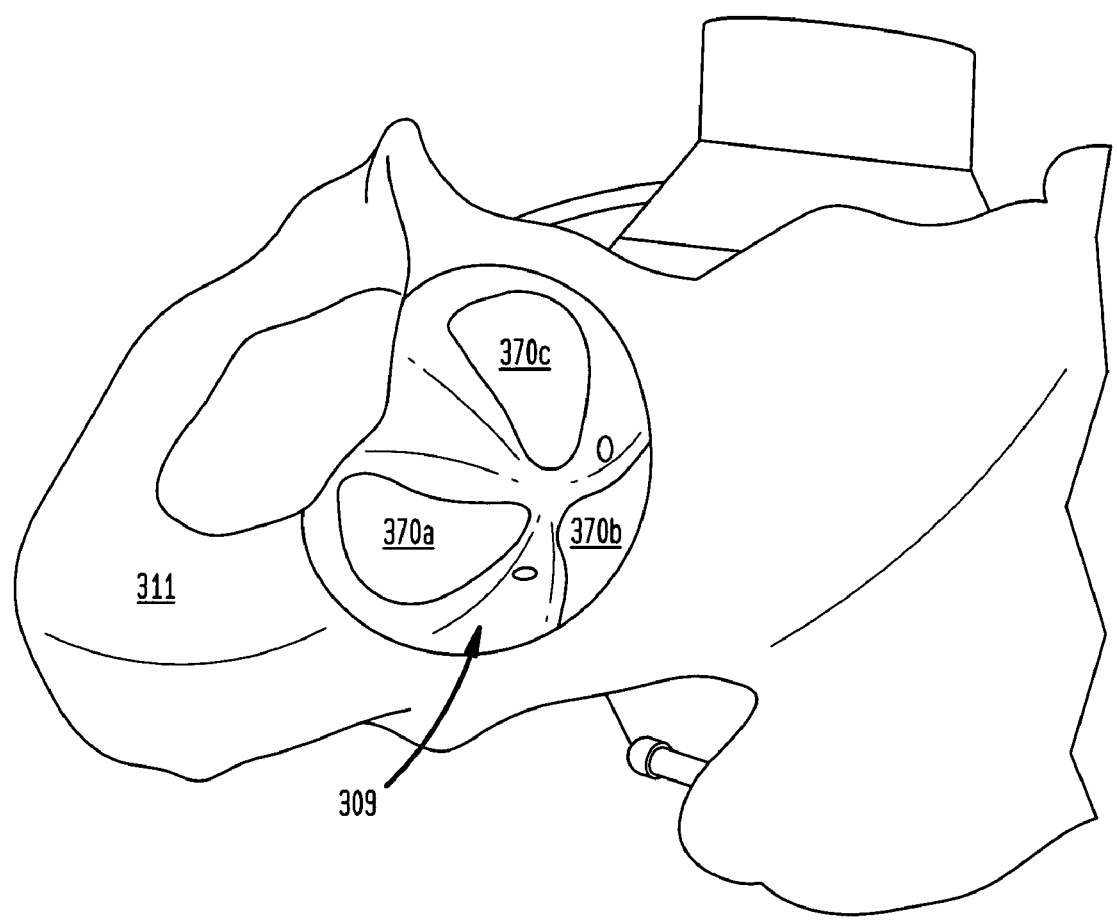
FIG. 17 is an illustration of a bone cavity after a surgical procedure using the bone-reaming system of FIG. 9 having a plurality of resurfacing implants therein.

The result of the use of bone-reaming system 300 is a surgically repaired bone cavity as shown in FIG. 17 where inserts 370 are secured within respective cut recesses 536 and are flush with the remaining outer surface of bone cavity 309. Bone cavity 309 is shown in a post-surgery state where the surface of bone cavity 309 can be seen to be substantially smooth and continuous.

Figure 18:
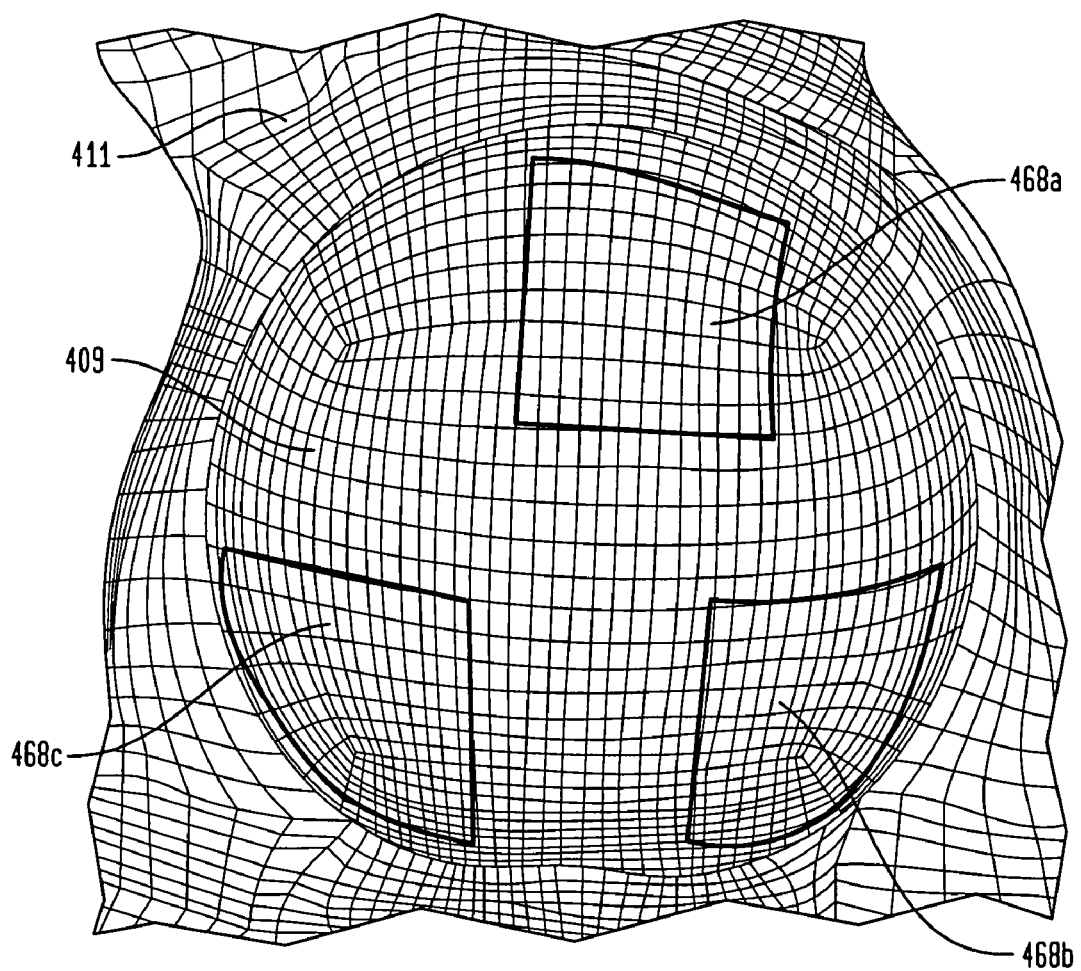
FIG. 18 is a graphical view of a bone cavity of a type which may be acted upon by the present invention.

A graphic illustration of a bone cavity 409 and a surrounding bone 411 is shown in FIG. 18. A first outline 468a, a second outline 468b, and a third outline 468c define portions of bone cavity 409 which need to be cut or removed. As can be seen, the shapes and sizes of the outlines are different. As such, an illustration such as that of FIG. 18 can be created for any possible configuration of a surgical procedure, whereby a corresponding routing guide can be manufactured and implanted. A bone-reaming system as contemplated with respect to the present invention may then be used to cut the portions of bone adjacent to outlines 468. Specifically, such outlines 468 may be utilized in machining or otherwise manufacturing a guide having cutouts corresponding to the areas desired to be repaired.

Figure 19:
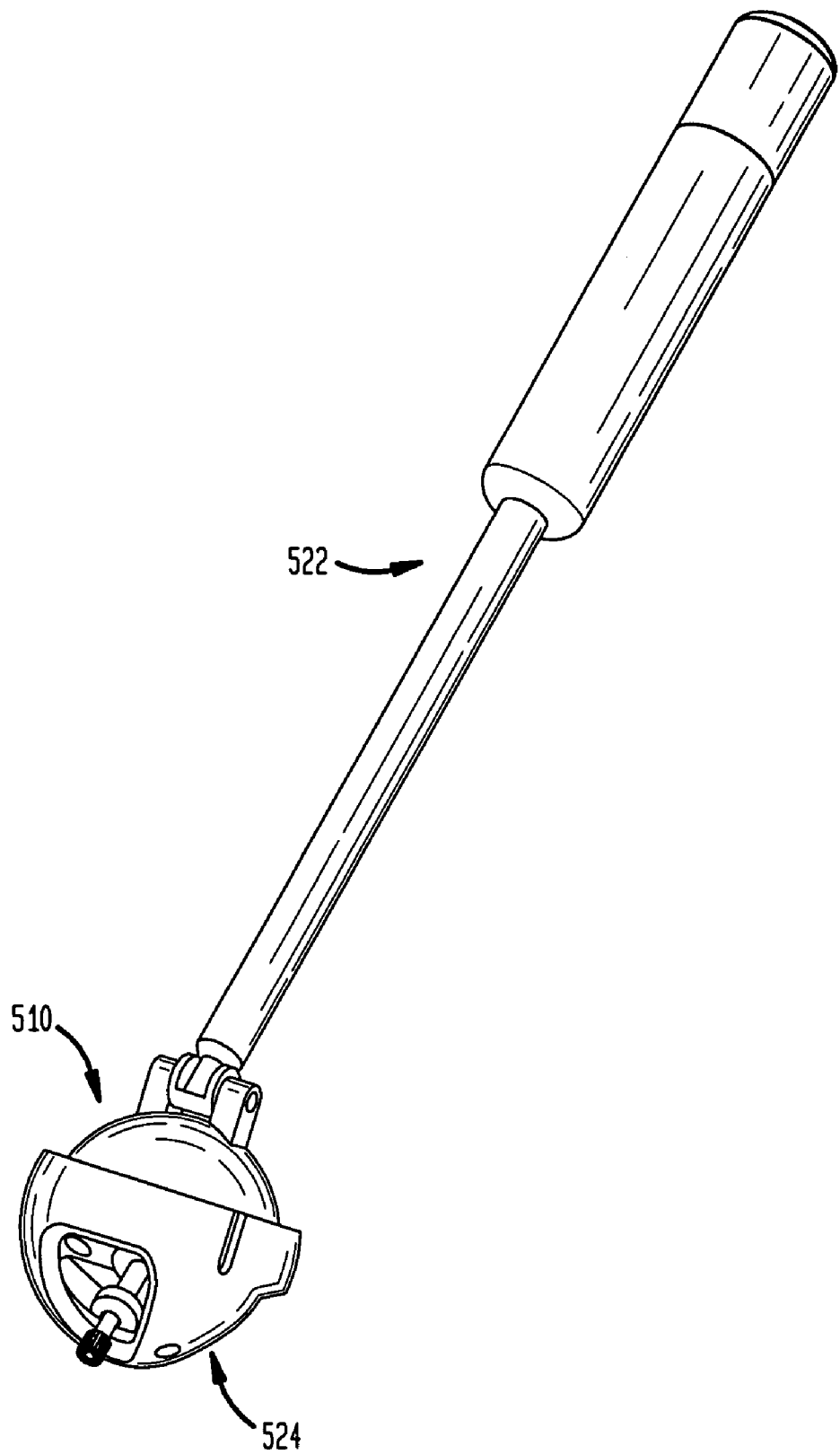
FIG. 19 is a perspective view of a bone-reaming system in accordance with a fourth embodiment of the present invention.

FIG. 19 depicts yet another embodiment of the present invention, bone-reaming system 500. As in the above-discussed embodiments, system 500 includes a cutting apparatus 510 pivotally connected to a handle 522, and a routing guide 524. Operation of system 500 is similar to that of the previously discussed embodiments. Where possible, like elements in system 500 have been accorded similar reference numerals as that of elements in the other embodiments of the present invention within the 500-series of numbers. It is to be understood that any of the variations of this fourth embodiment may be incorporated into any of the other embodiments, and likewise, any of the variations heretofore discussed may be incorporated into the present embodiment. Moreover, although not discussed in detail, the method of utilizing system 500 remains similar in nature to the above-discussed embodiments, with certain changes/additions being discussed below.

Figure 20:
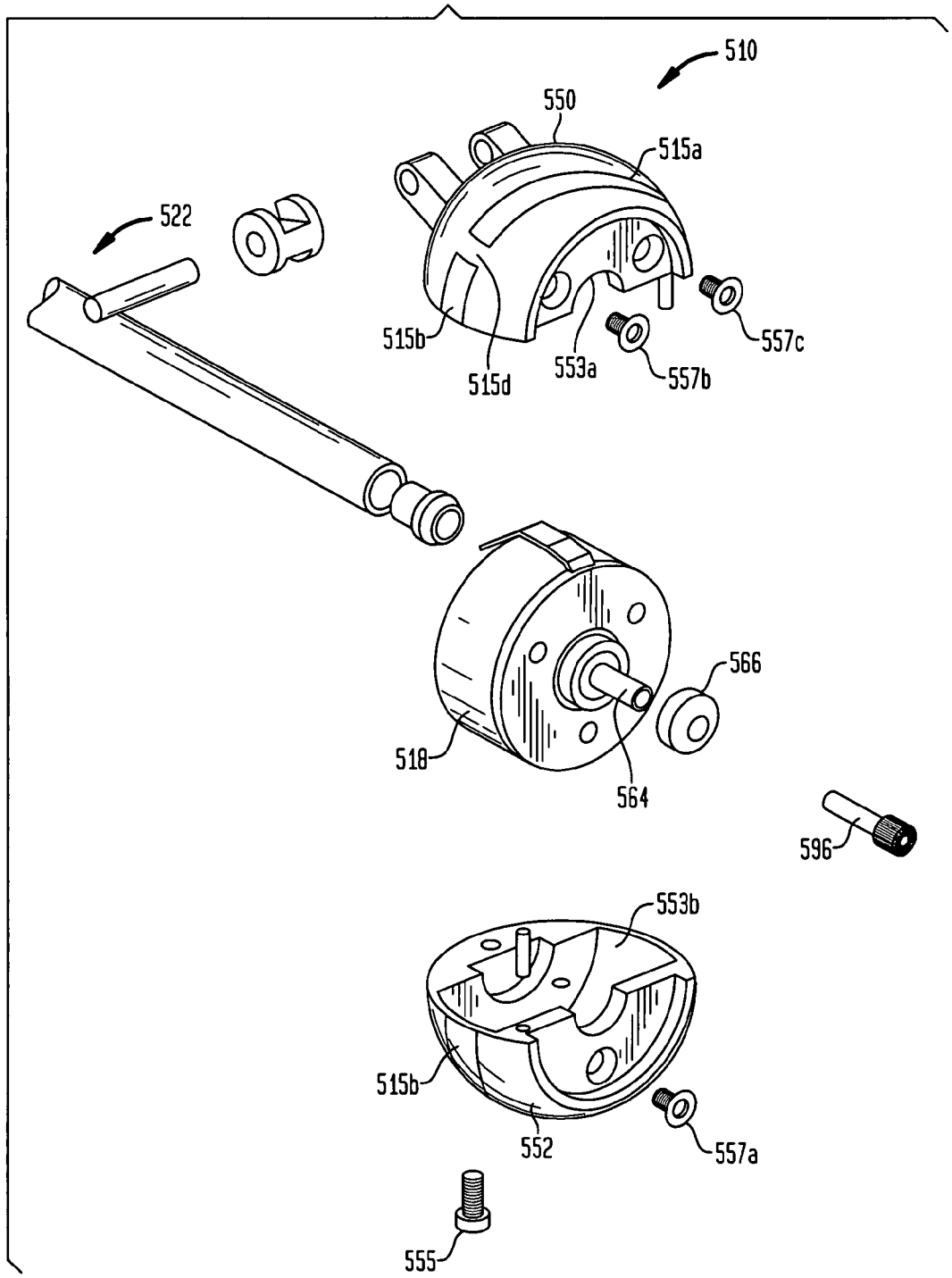
FIG. 20 is an exploded view of a portion of the bone-reaming system of FIG. 19.
Figure 21:
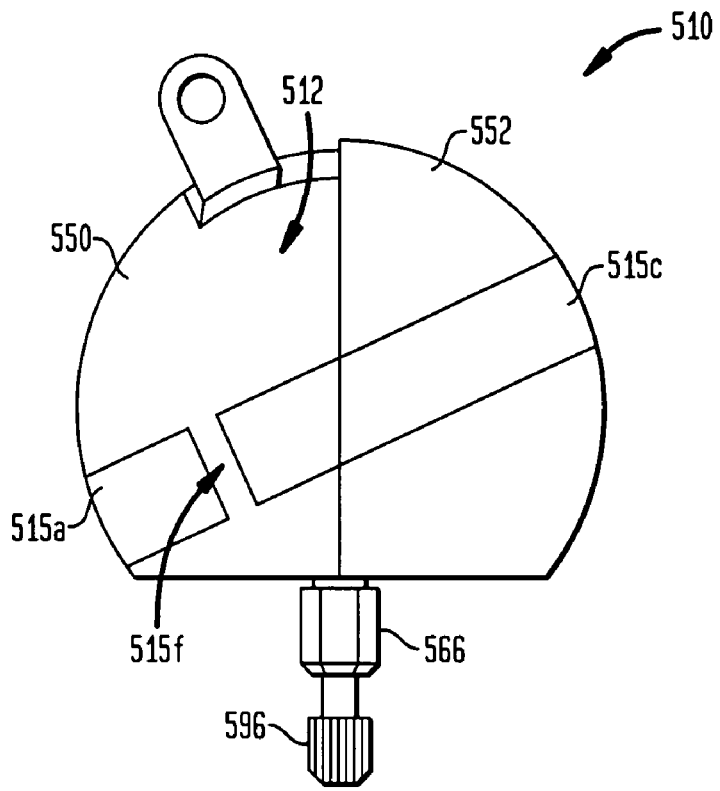
FIG. 21 is a side view of a cutting apparatus of the bone-reaming system of FIG. 19.
Figure 22:
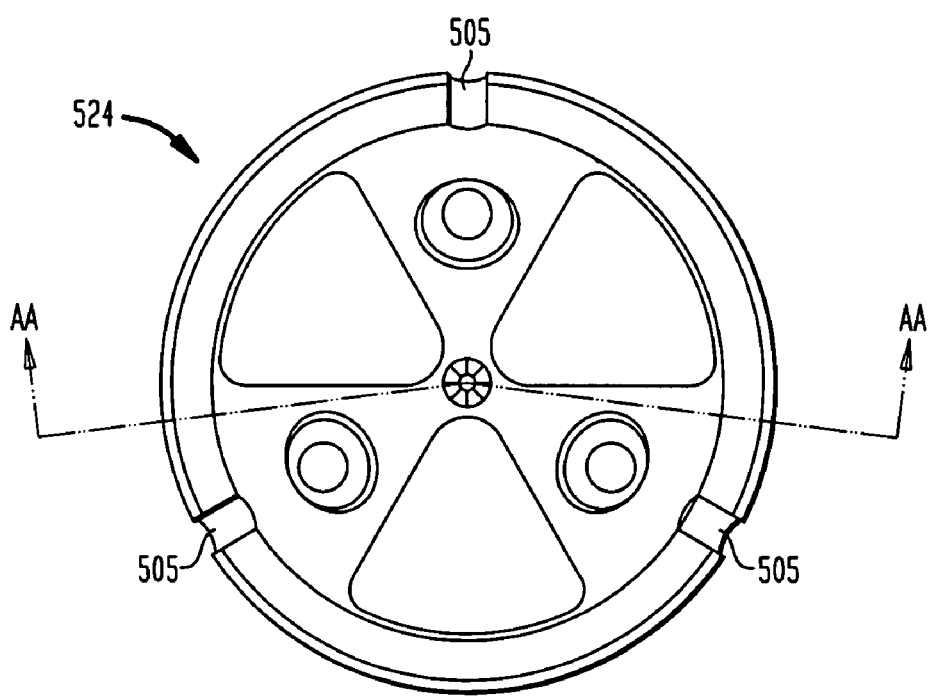
FIG. 22 is a top view of a routing guide of the bone-reaming system of FIG. 19.
Figure 23:
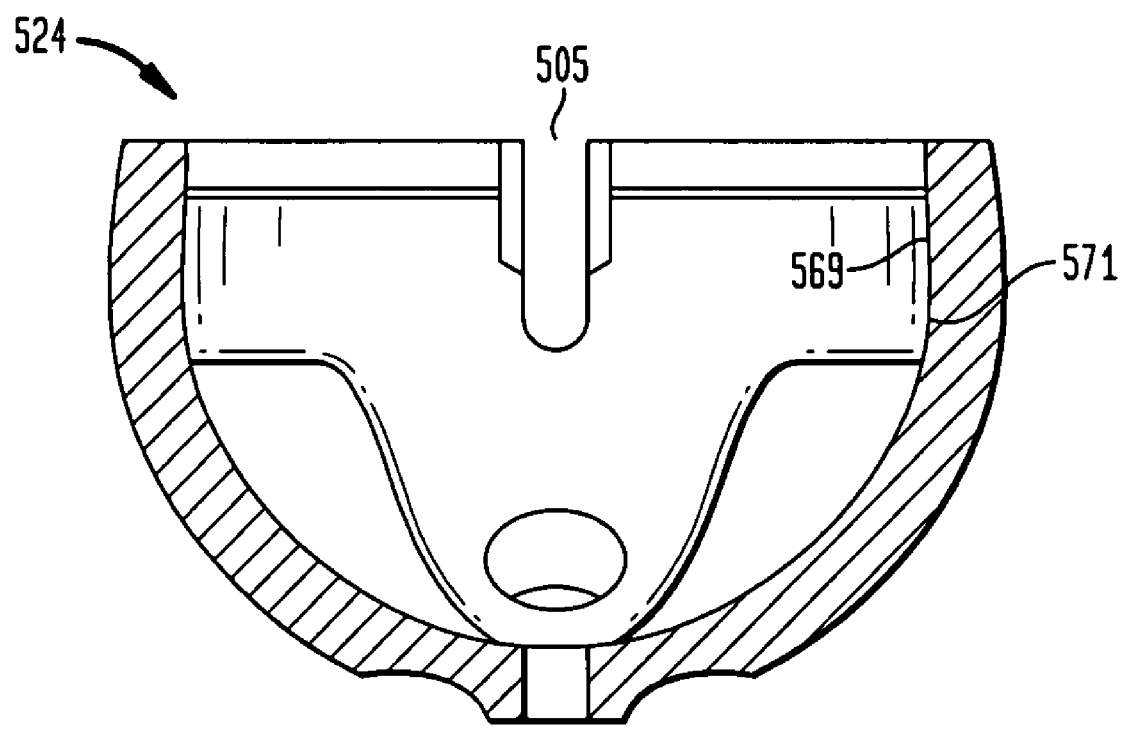
FIG. 23 is a cross sectional view of the routing guide of the bone-reaming system of FIG. 19, taken along line AA-AA of FIG. 22.

Cutting apparatus 510 is more clearly shown in the exploded view of FIG. 20. Two portions 550 and 552 are both preferably substantially hemispherical and together comprise housing 512. Disposed within housing 512, in a chamber formed by two cooperating hollow sections 553a and 553b formed in portions 550 and 552 respectively, is a motor 518. Portions 550 and 552 are connected to each other by elongate screw 555, and to motor 518 by three shorter screws 557a-c. Of course, other fixation elements may be employed. Cutting apparatus 510 also includes a burr 596 attached to an axle 564 by a locking ring 566. Preferably, this locking ring 566 includes a set screw (not shown), which when tightened, causes burr 596 to be effectively fixed to axle 564. However, other constructions may be utilized for this connection, such as cooperating tapered surfaces or mechanical connections such as glue or welding.

As is mentioned above, operation of system 500 is preferably similar to the above-described three other embodiments of the present invention. For example, although not specifically described, handle 522 is preferably capable of moving in one or more degrees of freedom with respect to cutting apparatus 510. Also, although not shown, motor 518 must be provided with a power source, which may be facilitated through the use of an electrical connection that may pass through handle 522. For example, a wire or ribbon connection may be disposed in the handle and connected to both a power source and the motor. However, system 500 does include certain additional elements heretofore not discussed in relation to the other embodiments. Tantamount to these additional elements is the inclusion of a keyed section 515 along the exterior surface of housing 512 and its cooperation with the structure of routing guide 524.

As is better shown in FIGS. 21-24, keyed section 515 includes three flattened areas 515a-c situated along an equator (the widest area) of housing 512. Because of the required ultimate orientation of burr 596, the equator is skewed with respect to the burr. The inclusion of three flattened areas 515a-c on the exterior surface of the circular shaped housing 512 essentially creates three protrusions 515d-f therebetween. These protrusions are in reality part of the natural equator of housing 512. Routing guide 524 includes three slots 505 (best shown in FIG. 22) for receiving protrusions 515d-f. Absent slots 505, lip extension 569 (best shown in FIG. 23) of routing guide 524 would not allow protrusions 515d-f to pass by, thereby preventing insertion of cutting apparatus 510 in guide 524. Lip extension 569 essentially creates an undercut 571 within the interior of guide 524. Once protrusions 515d-f pass below lip extension 569, they reside in undercut 571 and allow for movement of cutting apparatus 510 in routing guide 524. However, because of the extension of burr 596 from housing 512, the burr cannot be moved out of the particular one of the cutouts 526a-c of guide 524 it is initially inserted through. In other words, a surgeon or other medical professional must choose which one of cutouts 526a-c he or she would like to utilize to guide their cuts, and then must insert cutting apparatus 510 in guide 524 accordingly. In this regard, it is noted that in the embodiment shown in the figures, both protrusions 515d-f and slots 505 are situated every 120 degrees. However, any configuration may be employed, including the inclusion of more or less than three protrusions and/or slots.

Figure 24:
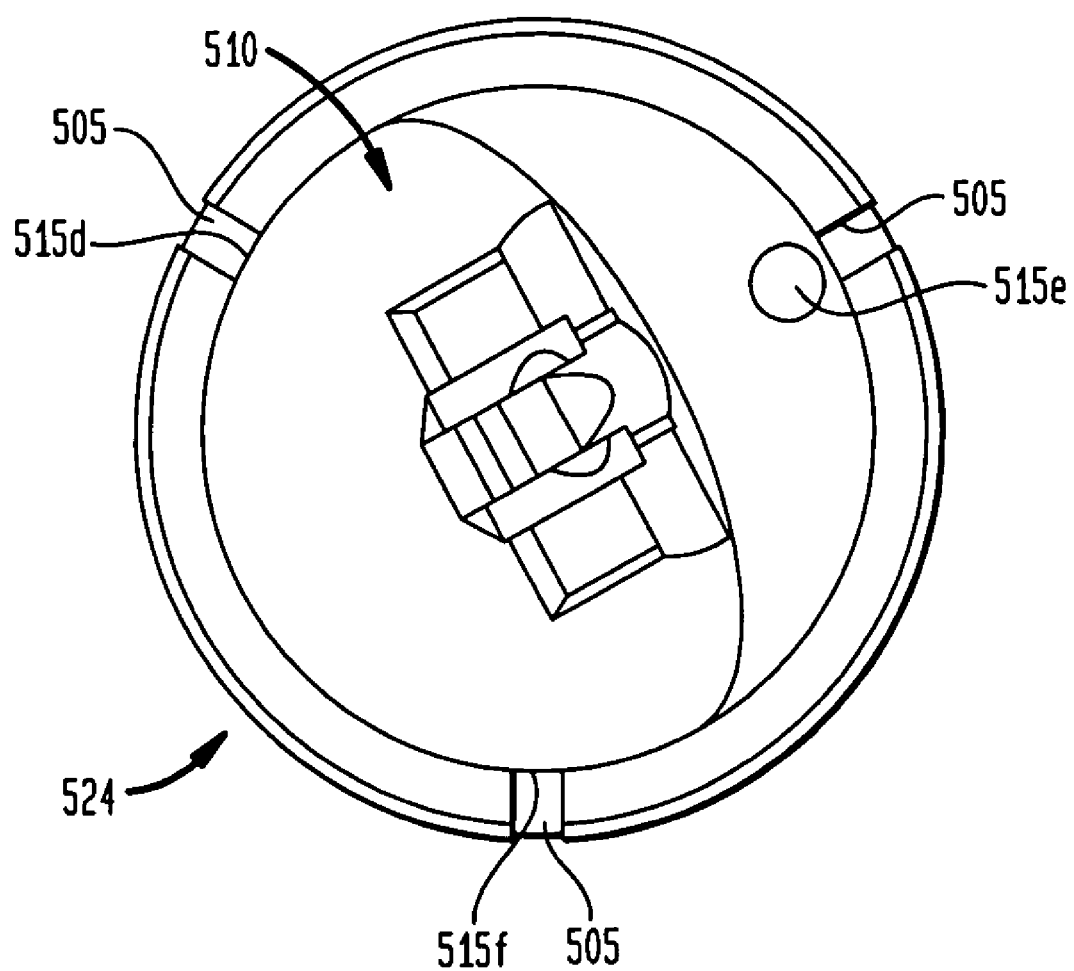
FIG. 24 is a top view of the bone-reaming system of FIG. 19, illustrating the cutting apparatus inserted in the routing guide.

A fully inserted cutting apparatus 510 in routing guide 524 is shown in FIG. 24. It is noted that the configuration of this fourth embodiment provides an assurance that cutting apparatus 510 cannot be inadvertently withdrawn from routing guide 524, and that only the desired portion of bone is cut through one of cutouts 526a-c. In use, a surgeon or other medical professional simply aligns protrusions 515d-f with the correct slots 505, so that burr 596 ultimately becomes disposed in the desired cutout 526a-c. Upon finishing the cutting operation, the protrusions are realigned with the slots and cutting apparatus 510 is removed from guide 524. The cutting apparatus 510 is then rotated in one direction or the other, so as to align protrusions 515d-f with the correct slots 505, so that burr 596 becomes disposed in the next desired cut out 526a-c. These steps are repeated until all desired cuts are made.

It is to be understood that the cooperation between the cutting apparatus and routing guide of this fourth embodiment may be employed in any of the above-described embodiments. It is also to be understood that those of ordinary skill in the art would readily recognize that this cooperation may be varied. For example, the size, shape and position of flattened areas 515a-c and protrusions 515d-f may be varied, as can that of slots 505, lip extension 569, and undercut 571. In addition, the size an shape of cutting apparatus 510 and routing guide 524 as a whole may be varied to allow for more or less movement of the apparatus when disposed within the guide.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of resurfacing a bone comprising the steps of:
providing a cutting apparatus comprising a housing having an aperture and a convex surface, a motor disposed within said housing, and a cutter attached to said motor and extendable through said aperture;
providing a routing guide having at least one cutout and a concave surface that is complementary to said convex surface of said housing;
removably securing said routing guide to a bone cavity;
inserting said cutting apparatus into said routing guide, so that at least a portion of said housing contacts said routing guide; and
manipulating said cutting apparatus within said routing guide by articulating said convex surface of said housing within said concave surface of said routing guide to allow said cutter to cut at least a portion of the bone cavity.

2. The method of claim 1, further comprising the step of removing said routing guide and said cutting apparatus.

3. The method of claim 1, further comprising the step of anchoring said routing guide with a stabilization means.

4. The method of claim 3, wherein said stabilization means are selected from the group consisting of spikes, screws, nails, cement or an adhesive.

5. The method of claim 1, wherein said housing is rotatable within said routing guide.

6. The method of claim 1, wherein the bone cavity has a concave surface.

7. The method claim 6, wherein the bone cavity is an acetabulum.

8. The method of claim 1, further including the step of aligning a keyed section of said housing with complimentary structure of said routing guide.

9. The method claim 8, wherein said keyed section includes three flattened sections disposed about an equator of said housing.

10. The method claim 1, wherein the manipulating step includes cutting at least a portion of the bone cavity through said at least one cutout to create at least one recess in a surface of the bone cavity, and further comprising the step of placing an insert within at least one of said at least one recesses.

11. The method of claim 10, further including the steps of providing an impact device, contacting a head of said impact device with said insert placed within said recess, and impacting said insert with said head of said impact device to further secure said insert within said recess of the bone cavity.

12. The method of claim 1, further including the steps of providing a drill guide, removably securing said drill guide to said routing guide, and drilling a hole into the bone through a guide hole in said drill guide.

13. The method of claim 12, further comprising the steps of providing an insert and placing a protrusion of said insert into said guide hole.

14. A method of providing instrumentation, inserts, and information for a procedure of resurfacing a bone, the method comprising the steps of:
providing a cutting apparatus comprising a housing having an aperture and a convex surface, a motor disposed within said housing, and a cutter attached to said motor and extendable through said aperture;
providing a routing guide having at least one cutout and a concave surface that is complementary to said convex surface of said housing; and
providing a surgeon with information on a method to perform the procedure of resurfacing the bone using the cutting apparatus and the routing guide, the method including:
removably securing said routing guide to a bone cavity;
inserting said cutting apparatus into said routing guide, so that at least a portion of said housing contacts said routing guide; and
manipulating said cutting apparatus within said routing guide by articulating said convex surface of said housing within said concave surface of said routing guide to allow said cutter to cut at least a portion of the bone cavity.

15. The method of claim 14, wherein the step of providing a surgeon with information on a method to perform the procedure includes providing information on the step of removing said routing guide and said cutting apparatus.

16. The method of claim 14, wherein the step of providing a surgeon with information on a method to perform the procedure includes providing information on the step of anchoring said routing guide with a stabilization means.

17. The method of claim 16, wherein said stabilization means are selected from the group consisting of spikes, screws, nails, cement or an adhesive.

18. The method of claim 14, wherein said housing is rotatable within said routing guide.

19. The method of claim 14, wherein the bone cavity has a concave surface.

20. The method claim 19, wherein the bone cavity is an acetabulum.

21. The method of claim 14, wherein the step of providing a surgeon with information on a method to perform the procedure includes providing information on the step of aligning a keyed section of said housing with complimentary structure of said routing guide.

22. The method claim 21, wherein said keyed section includes three flattened sections disposed about an equator of said housing.

23. The method claim 14, wherein the manipulating step includes cutting at least a portion of the bone cavity through said at least one cutout to create at least one recess in a surface of the bone cavity, and wherein the step of providing a surgeon with information on a method to perform the procedure includes providing information on the step of placing an insert within at least one of said at least one recesses.

24. The method of claim 23, further including the step of providing an impact device, and wherein the step of providing a surgeon with information on a method to perform the procedure includes providing information on the steps of contacting a head of said impact device with said insert placed within said recess and impacting said insert with said head of said impact device to further secure said insert within said recess of the bone cavity.

25. The method of claim 14, further including the step of providing a drill guide, and wherein the step of providing a surgeon with information on a method to perform the procedure includes providing information on the steps of removably securing said drill guide to said routing guide and drilling a hole into the bone through a guide hole in said drill guide.

26. The method of claim 25, wherein the step of providing a surgeon with information on a method to perform the procedure includes providing information on the steps of providing an insert and placing a protrusion of said insert into said guide hole.

* * * * *